United States Patent
Rooney et al.

(10) Patent No.: US 12,352,204 B2
(45) Date of Patent: Jul. 8, 2025

(54) PYROLYSIS PRODUCT COMPRESSION USING CO₂ LOOP

(71) Applicant: ExxonMobil Chemical Patents Inc., Baytown, TX (US)

(72) Inventors: Mark A. Rooney, Pasadena, TX (US); Paul F. Keusenkothen, Houston, TX (US)

(73) Assignee: ExxonMobil Engineering & Technology Company, Baytown, TX (US)

( * ) Notice: Subject to any disclaimer, the term of this patent is extended or adjusted under 35 U.S.C. 154(b) by 444 days.

(21) Appl. No.: 17/782,679

(22) PCT Filed: Dec. 18, 2020

(86) PCT No.: PCT/US2020/066161
§ 371 (c)(1),
(2) Date: Jun. 6, 2022

(87) PCT Pub. No.: WO2021/138093
PCT Pub. Date: Jul. 8, 2021

(65) Prior Publication Data
US 2023/0027105 A1    Jan. 26, 2023

Related U.S. Application Data

(60) Provisional application No. 62/954,775, filed on Dec. 30, 2019.

(30) Foreign Application Priority Data

Apr. 6, 2020 (EP) .................................. 20168288

(51) Int. Cl.
*F02C 3/22* (2006.01)
*C10G 9/00* (2006.01)
(Continued)

(52) U.S. Cl.
CPC ................ *F02C 3/22* (2013.01); *C10G 9/002* (2013.01); *F02C 1/10* (2013.01); *F02C 3/10* (2013.01); *C10G 2300/4012* (2013.01)

(58) Field of Classification Search
CPC ..... F02C 3/10; F02C 3/22; F02C 1/10; C10G 9/002; C10G 2300/4006;
(Continued)

(56) References Cited

U.S. PATENT DOCUMENTS 3,365,387 A   1/1968   Cahn et al.
3,576,603 A   4/1971   Smith et al.
(Continued)

FOREIGN PATENT DOCUMENTS

EP         0008166 A1      2/1980
JP         2000-204965 A   7/2000
(Continued)

OTHER PUBLICATIONS

Allam power cycle, Wikipedia, Retrieved from URL: <https://en.wikipedia.org/wiki/Allam_power_cycle>, pp. 1-10.
(Continued)

*Primary Examiner* — In Suk C Bullock
*Assistant Examiner* — Jason Y Chong

(57) ABSTRACT

Processes, systems, and apparatus are provided for producing a compressed process gas comprising light olefin such as ethylene. The process utilizes a pyrolysis reactor to produce the process gas. A power generator utilizes a turbine operated based on an Allam cycle to produce shaft power for operating one or more compressors involved in processing of the process gas while producing a reduced or minimized amount of $CO_2$ that is released as a low-pressure gas phase product. Examples of using the shaft power for processing of the process gas can include compressing the process gas a process gas compressor powered by the produced shaft (Continued)

power and cooling the process gas using a refrigeration compressor powered by the produced shaft power.

18 Claims, 5 Drawing Sheets

(51) Int. Cl.
  *F02C 1/10* (2006.01)
  *F02C 3/10* (2006.01)
(58) Field of Classification Search
  CPC ............ C10G 2300/4012; Y02P 30/40; C07C 29/106; C07D 301/08; F05D 2210/00
  See application file for complete search history.

(56) References Cited

U.S. PATENT DOCUMENTS

| | | | |
|---|---|---|---|
| 4,287,377 | A | 9/1981 | Maslin et al. |
| 5,669,216 | A | 9/1997 | Ankersmit et al. |
| 5,763,691 | A | 6/1998 | Kawabe et al. |
| 7,815,873 | B2 | 10/2010 | Sankaranarayanan et al. |
| 7,846,401 | B2 | 12/2010 | Hershkowitz et al. |
| 7,943,808 | B2 | 5/2011 | Hershkowitz et al. |
| 8,596,075 | B2 * | 12/2013 | Allam .................. F02C 3/20 60/39.5 |
| 8,754,276 | B2 | 6/2014 | Buchanan et al. |
| 8,864,977 | B2 | 10/2014 | Spicer |
| 9,126,882 | B2 | 9/2015 | Lattner et al. |
| 9,187,382 | B2 | 11/2015 | Hershkowitz et al. |
| 9,322,549 | B2 | 4/2016 | Hershkowitz et al. |
| 9,346,728 | B2 | 5/2016 | Keusenkothen et al. |
| 2006/0260321 | A1 | 11/2006 | Minkkinen et al. |
| 2007/0144940 | A1 | 6/2007 | Hershkowitz et al. |
| 2007/0261991 | A1 | 11/2007 | Beattie et al. |
| 2008/0210598 | A1 | 9/2008 | Annamalai et al. |
| 2008/0300438 | A1 | 12/2008 | Keusenkothen et al. |
| 2011/0112314 | A1 | 5/2011 | Chewter et al. |
| 2012/0067056 | A1 | 3/2012 | Palmer et al. |
| 2012/0144837 | A1 | 6/2012 | Rasmussen et al. |
| 2013/0157205 | A1 | 6/2013 | Hershkowitz et al. |
| 2014/0163273 | A1 | 6/2014 | Keusenkothen et al. |
| 2014/0163287 | A1 | 6/2014 | Keusenkothen et al. |
| 2014/0303339 | A1 | 10/2014 | Keusenkothen et al. |
| 2014/0303416 | A1 | 10/2014 | Keusenkothen et al. |
| 2014/0378728 | A1 | 12/2014 | Davis et al. |
| 2015/0166430 | A1 | 6/2015 | Keusenkothen et al. |
| 2015/0197696 | A1 | 7/2015 | Keusenkothen et al. |
| 2016/0176781 | A1 | 6/2016 | Hershkowitz et al. |
| 2017/0058712 | A1 | 3/2017 | Allam et al. |
| 2019/0169510 | A1 | 6/2019 | Pavia et al. |

FOREIGN PATENT DOCUMENTS

| | | |
|---|---|---|
| WO | 2010/077461 A1 | 7/2010 |
| WO | 2021/138093 A3 | 8/2021 |

OTHER PUBLICATIONS

Reliable power for a low-carbon future, Netpower, Retrieved from URL :<https://netpower.com/>, pp. 1-2.
Breaking ground for a groundbreaker: The first Allam Cycle power plant, Modern Power System, Retrieved from URL: <https://www.modernpowersystems.com/features/featurebreaking-ground-for-a-groundbreaker-the-first-allam-cycle-power-plant-4893271/>, 2016, pp. 1-4.
U.S. Appl. No. 62/611,863, "Coke Mitigation In Hydrocarbon Pyrolysis" filed Dec. 29, 2017, 20 Pages.
U.S. Appl. No. 62/806,274, "Processes And Apparatus For The Removal Of Coke And Tar From A Furnace Effluent" filed Feb. 15, 2015, 15 Pages.
U.S. Appl. No. 62/821,133, "Processes for On-Stream Decoking" filed Mar. 20, 2019, 14 Pages.
Extended European Search Report received for European Patent Application No. 20168288.7 mailed on Oct. 5, 2020, 10 Pages.
International Preliminary Report on Patentability received for PCT Application No. PCT/US2020/066161, mailed on Jul. 14, 2022, 11 Pages.
International Search Report and Written Opinion received for PCT Application No. PCT/US2020/066161, mailed on Jun. 23, 2021, 17 Pages.
Allam R. J., (2013) "NET Power's CO2 cycle: the breakthrough that CCS needs", Modern Power System, Retrieved from URL :<https://www.modernpowersystems.com/features/featurenet-powers-co2-cycle-the-breakthrough-that-ccs-needs/>, pp. 1-7.
Williamson, K. D., (2019) "Gassing Up", National Review, Retrieved from URL: <https://www.nationalreview.com/2019/03/natural-gas-energy-production-cleaner/>, pp. 1-3.

* cited by examiner

PYROLYSIS PRODUCT COMPRESSION USING $CO_2$ LOOP

CROSS-REFERENCE TO RELATED APPLICATIONS

This application is a US national phase application of PCT Application Serial No. PCT/US2020/066161 having a filing date of Dec. 18, 2020, which claims priority to and the benefit of U.S. Provisional Application No. 62/954,775 having a filing date of Dec. 30, 2019 and European Patent Application No. 20168288.7 having a filing date of Apr. 6, 2020, the disclosures of all of which are incorporated herein by reference in their entireties.

TECHNICAL FIELD

The invention relates to pyrolysis product compression using shaft power produced in a power generator while reducing or minimizing exhaust emissions, e.g., of $CO_2$. The invention also relates to processes, systems, and apparatus for carrying out the pyrolysis, the power generation, and the compression.

BACKGROUND

Olefinic compounds are a class of hydrocarbon compounds which have at least one double bond of four shared electrons between two carbon atoms. In part as a result of their utility as feeds for producing desirable products, olefin demand continues to grow, particularly for light olefin such as ethylene, propylene, and butenes.

Light olefin is typically manufactured in an olefins plant (e.g., an ethylene plant) which includes production and recovery facilities. In certain conventional olefins plants, the olefin production facility includes one or more steam cracker furnaces for steam cracking hydrocarbon-containing feeds. A steam cracker furnace generally includes a convection section and a radiant section. The radiant section includes a plurality of tubular members which are typically referred to as "radiant tubes". The radiant tubes are located proximate to one or more fired heaters, e.g., burners, in the radiant section which heat the outer surface of the furnace tubes. Hot combustion gases exit the radiant section and are introduced into the convection section. The convection section also includes tubular members, typically referred to as "convection tubes". The hot gases from the radiant section heat the outer surfaces of the convection tubes and then exit the convection section.

Conventional steam cracking processes typically produce light olefin by hydrocarbon pyrolysis during pyrolysis mode. Coke and other deposits which form during pyrolysis mode are removed from the furnace internals during regeneration (decoking) mode. During pyrolysis mode, a hydrocarbon-containing feed is introduced into the convection tubes for feed preheating. Feed preheating is carried out in segments of the convection tubes located in an upper region of the convection section. Steam is combined with the preheated feed, and the steam-feed mixture is further heated in segments of the convection tubes located in a lower region of the convection section. The heated feed-steam mixture is introduced into the heated furnace tubes in the radiant section, and heat transferred from the furnace tube to the mixture results in the pyrolysis of at least a portion of the feed to produce a process gas comprising light olefin. During regeneration mode, a flow of oxygenate-containing decoking fluid (e.g., a gaseous steam-air mixture) is substituted for the hydrocarbon-containing feed, and the burners continue to heat the radiant and convection sections. The decoking fluid is conducted through the heated convection tubes, heated radiant tubes, and associated furnace piping, internals, etc., to at least partly remove deposited coke. After sufficient coke removal is achieved, the steam cracking furnace is returned to pyrolysis mode operation.

In certain steam cracking processes, e.g., those disclosed in U.S. Patent Application Publication No. 2007-0261991, the process gas is cooled by an indirect transfer of heat from the process gas to water in one or more transfer line heat exchangers ("TLE"). Saturated steam from the TLE is conducted to a steam drum. Condensed water in the steam drum is recycled to the TLE, typically via thermo-syphoning. Saturated steam can be conducted away from the steam drum to processing equipment located in the olefins plant and elsewhere, with condensed water make-up obtained from a suitable source. For example, saturated steam can be conducted away from the steam drum for superheating in one or more superheater tubes positioned between segments of the convection coils.

To lessen the difficulties associated with separating products such as ethylene from the process gas, the cooled process gas is typically compressed in a process gas compressor located in the olefin plant's recovery facility. U.S. Patent Application Publication No. 2008-0210598 discloses using shaft power derived from a steam turbine to power the process gas compressor. Superheated steam exiting the convection section's superheater coils is utilized as a steam source for the steam turbine.

Although this method is effective for powering the process gas compressor, the steam cracker furnace's thermal efficiency is decreased because additional furnace firing is needed to superheat the saturated steam, e.g., furnace firing beyond that needed to produce the process gas. Another difficulty encountered when carrying out the method results from variations in the temperature and pressure of the superheated steam that typically occur during steam cracking. As a result of effects such as radiant tube coking, the amount of furnace firing needed to produce the process gas is greater at the end of the steam cracking process than at its start. As disclosed in P.C.T. Patent Application No. WO 2010-077461, water can be introduced into the superheater coil to at least partially overcome this difficulty by de-superheating the steam. The amount of water supplied to the de-superheater is controlled to prevent damage to the steam turbine. This benefit is obtained, however, at a further loss in the furnace's thermal efficiency resulting from the additional furnace firing needed to vaporize the de-superheater water.

Since process gases from a plurality of steam cracking furnaces are typically combined upstream of the process gas compressor, another difficulty arises when one or more furnaces is unexpectedly taken off-line, e.g., by decreasing or halting the amount of furnace firing. Since decreasing steam turbine shaft power can damage the process gas compressor, commercial steam cracking facilities typically include additional steam generators which continuously produce additional superheated steam. The additional superheated steam is substituted for a steam cracker furnace's superheated steam when the furnace is unexpectedly taken off line. Although the risk of compressor damage is lessened, the additional steam generators further decrease the olefin plant's thermal efficiency.

Another operational difficulty results from the coupling (via the superheated steam) of the olefin production facility's steam cracking furnaces and olefin recovery facility.

Since these facilities are coupled, modification of the steam cracking furnaces, e.g., in order to increase the amount of process gas produced by the furnaces, is made more difficult by a corresponding need to modify the steam-driven power cycle in the recovery facility.

In order to at least partly overcome these difficulties, proposals have been made to obtain power for the process gas compressor from a power source external to the olefin production facility, such as from a gas turbine powering an electric generator, which in turn powers an electric motor providing shaft power to the process gas compressor. However, directly driving a process gas compressor with shaft power produced by a "stand-alone" gas turbine is reported to be infeasible, e.g., as a result the gas turbine's shorter maintenance schedule compared to that of a typical steam cracker furnace. The low thermal efficiency of a typical gas turbine also leads to a decrease in the olefin plant's overall thermal efficiency.

There is therefore a need for more thermally-efficient olefin production plants, particularly those which decouple the plant's production and recovery facilities.

U.S. Patent Application Publication 2019/0169510 describes systems and methods for decoupling the production and recovery facilities for an olefin plant.

A closed loop cycle sometimes called the "Allam cycle" is described in U.S. Patent Application Publications 2012/0067056 and 2017/0058712 for powering a turbine using $CO_2$ as a working fluid. The Allam cycle is described as provide electric power through natural gas fuel with reduced $CO_2$ emissions.

A modern olefins production plant consumes a large amount of shaft power to drive various compressors and pumps. Energy efficiency improvement in power production for the plant is highly desirable. For example, the process gas compressor discussed in earlier paragraphs can be very large requiring significant amount of shaft power to drive. Additionally, the compressors used in refrigeration units in the olefins production plant can consume large amount of shaft power as well.

From the product recovery section of a typical steam cracker olefins production plant, a large quantity of "tail gas" comprising methane and optionally hydrogen is typically produced. The tail gas is typically combusted as fuel to provide energy, in which process $CO_2$ and water are produced. It would be highly desirable that the energy released from the combustion of the tail gas can be used to power the process steps in the olefins production plant, the $CO_2$ produced can be concentrated, captured, stored, and/or utilized, and the water produced can be used, in an efficient manner There are, however, significant challenges in achieving one, let alone, two or all of these goals.

An olefins production plant including a steam cracker is desirably located close to a user of the olefin products, e.g., polyethylene and/or polypropylene production facilities to minimize the transportation of the olefins. For olefins production plants located close to the source of the hydrocarbon feed and far to the users, it may be highly desirable to convert one or more of the olefin products into a chemical easier to transport in a conversion plant in close proximity to the olefins production plant. It would be highly desirable that the operations of the steam cracker and the recovery section in the olefins production plant, the conversion plant, and a power production plant, if any, including tail gas combustion are integrated to provide a high level of energy efficiency.

This disclosure meets these and other needs.

SUMMARY

The invention is based in part on integration of the effluent processing train for a pyrolysis reactor with a turbine operated based on an Allam cycle. The turbine can be used to provide shaft power for the process gas compressor, refrigeration compressors, and/or other portions of the effluent processing train. By powering one or more portions of the effluent processing train using a separate turbine operated based on an Allam cycle, the operation of the processing train can be decoupled from operation of the pyrolysis reactor while also reducing or minimizing emission of $CO_2$ and/or other greenhouse gases. This can be beneficial, for example, in configurations where a plurality of pyrolysis reactors are used to jointly feed a smaller plurality of effluent processing trains. By providing an independent power source for the effluent processing trains, the efficiency of the overall system can be maintained when one or more of the pyrolysis reactors is taken off-line.

DETAILED DESCRIPTION

Overview

Figure 1:
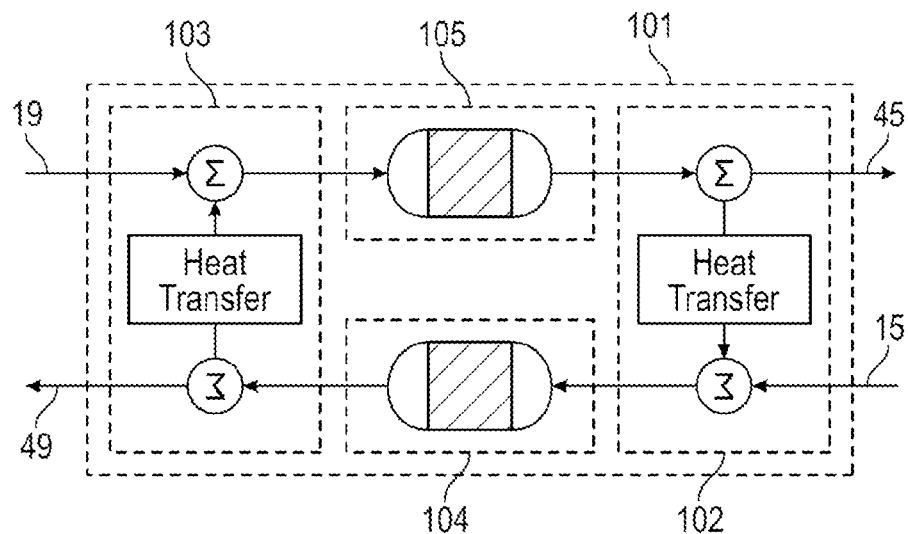
FIG. 1 conceptually shows transfers of heat that can occur in a regenerative reverse-flow pyrolysis reactor during regeneration mode (top) and pyrolysis mode (bottom).

Certain aspects of the invention relate to processes, systems, and apparatus are provided for producing a compressed process gas comprising light olefin such as ethylene. The process utilizes a pyrolysis reactor, e.g., a tubular flow-through reactor, to produce the process gas. A power generator utilizes a turbine operated based on an Allam cycle to produce shaft power for operating one or more compressors involved in processing of the process gas while producing a reduced or minimized amount of $CO_2$ that is released as a low-pressure gas phase product. Examples of using the shaft power for processing of the process gas can include compressing the process gas a process gas compressor powered by the produced shaft power and cooling the process gas using a refrigeration compressor powered by the produced shaft power.

Using a turbine that is operated based on the Allam cycle to power the process gas compressor can provide a variety of advantages. Conventionally, many pyrolysis reactors use steam generated as a by-product of the pyrolysis process to power a turbine, which then provides power for the process gas compressor. While this can be effective, this couples operation of the process gas compressor with the pyrolysis process. Using a separate turbine to power the process gas compressor allows the process gas compressor to operate independently from the pyrolysis process.

A difficulty with using a separate turbine to power the process gas compressor is the potential increase in greenhouse gas and other atmospheric emissions that comes from operating a separate fuel combustion process. The potential emissions from using a separate turbine can include $CO_2$, $NO_x$, $SO_x$, $NH_3$, and particulate matter. In various aspects, this difficulty is reduced or minimized by using a turbine that is operated based on the Allam cycle. In an Allam cycle, the combustion process that provides energy for the turbine also supplies $CO_2$ that is used as a working fluid. The $CO_2$ is maintained at sufficient temperature and pressure during the cycle so that the $CO_2$ remains substantially in a supercritical state, and therefore phase changes do not occur. This reduces or minimizes energy losses due to evaporation or condensation of the working fluid. Additionally, as new $CO_2$ is generated, a portion of the existing compressed $CO_2$ in the working fluid can be withdrawn. If a relatively pure oxygen stream is used as the oxidant for combustion, the resulting withdrawn $CO_2$ can also have high purity. This can allow the withdrawn $CO_2$ to be suitable for sequestration or other uses without having to perform a separation on the withdrawn $CO_2$ to remove nitrogen. In addition, using a relatively pure oxygen stream to minimize or eliminate nitrogen from the flue gas can also reduce, minimize, or eliminate $NO_x$ emissions (as well as $NH_3$ emissions that can be produced by $NO_x$ reduction systems). Thus, using a turbine operated based on an Allam cycle can provide independent operation of the process gas compressor while also reducing or minimizing the amount of $CO_2$ that is either exhausted to the atmosphere or that requires capture in a separate post-processing step.

Additionally, certain features of regenerative reverse-flow thermal pyrolysis reactors make this form of reactor particularly suitable for producing the process gas. Unlike steam cracking furnaces, heat is recovered within the reverse-flow thermal pyrolysis reactor, and the recovered heat is stored by reactor components during both regeneration mode and pyrolysis mode operation. Heat recovered and stored in the reactor during pyrolysis mode is available for subsequent heat transfer to process streams during regeneration mode, e.g., for heat transfer to fuel and/or air. This transfer lessens the amount of heat that would otherwise need to be supplied to the reactor during regeneration mode, as would be the case in a steam cracker furnace operating in regeneration mode. Heat recovered and stored in the reactor during regeneration mode is available for a transfer of heat during a subsequent pyrolysis mode, which decreases or entirely obviates the need for furnace heating during pyrolysis mode operation. Transferring heat away from the reactor to fuel and/or air during combustion mode cools that region of the reactor which is used for quenching the pyrolysis product during pyrolysis mode. This reactor cooling beneficially lessens or entirely obviates the need for external quenching (e.g., in one or more TLEs) of the pyrolysis product. Since TLEs are typically not needed when utilizing regenerative reverse-flow thermal pyrolysis reactors, the power generator and pyrolysis reactor can be substantially energetically-independent. An energetically-independent power generator is desirable because it at least partially overcomes the difficulties associated with increased or decreased compressor power requirements in response, e.g., to unexpected reactor outages, increases or decreases in process gas yields, etc. Certain desirable features of regenerative reverse-flow thermal pyrolysis reactors will now be explained in more detail with reference to FIG. 1.

Conceptually, regenerative reverse-flow thermal pyrolysis reactor 101 encompasses first 102 and second 103 heat transfer zones, a pyrolysis zone 104, and a combustion zone 105. These zones are shown schematically in FIG. 1 when the reactor operates in combustion mode (upper part of figure) and pyrolysis mode (lower part of figure). The figure is conceptual in that, e.g., the pyrolysis zone and combustion zone can occupy substantially the same (or overlapping) physical space within the reactor, albeit at different times. Methods used to establish initial conditions in these zones at the start of operation are not critical. For example, if the reactor is to begin in pyrolysis mode, conventional methods can be used to preheat the reactor's first heat transfer zone and precool the second heat transfer zone, but the invention is not limited thereto. During pyrolysis mode, which operates in forward flow (substantially from right to left as shown in the figure), heat is transferred from the reactor to the feed in the first heat transfer zone. Sufficient heat is transferred in the first heat transfer zone to pyrolyse the heated feed in the pyrolysis zone. The pyrolysis product is cooled by a transfer of heat from the pyrolysis effluent to the reactor in the second heat transfer zone, which rapidly quenches the pyrolysis product. Condensable constituents that may be present in the pyrolysis product typically deposit in the second heat transfer zone. The process gas, which typically comprises the remainder of the pyrolysis product, is conducted away via line 49 as shown. A useful feature of regenerative reverse-flow thermal pyrolysis reactors is that at least part of the heat removed from the pyrolysis product during the quenching (less any radiative, conductive, and convective losses) is stored in the reactor's second heat transfer zone and is available for transfer during regeneration mode operation. Another useful feature is that at least part of the heat removed from the combustion effluent during the quenching (again, less any radiative, conductive, and convective losses) is stored in the reactor's first heat transfer zone and is available for transfer during pyrolysis mode operation. These features are illustrated schematically in FIG. 1.

During regeneration mode, which is carried out in reverse-flow (e.g., substantially from left to right, as shown), oxidant and fuel are introduced into the reactor via line 19, which typically comprises substantially separate fuel channels and oxidant channels. The fuel and oxidant are conveyed through the second heat transfer zone toward the combustion zone. Sufficient heat is transferred from the reactor in the second heat transfer zone to the fuel and air for these to combust in the combustion zone. Heat is transferred from the combustion effluent to reactor the first heat transfer zone. Thus, the first and second heat transfer zones are regenerated for a following forward-flow thermal pyrolysis interval.

It is not necessary that both the fuel and oxidant be heated in the second heat transfer zone to carry out the combustion. The other (non-heated) component can be introduced into the combustion zone by way of one or more bypass lines (not shown). Typically, at least the oxidant is heated in the second heat transfer zone during combustion mode in order to oxidize and remove at least a portion of any combustible deposits remaining from previous pyrolysis mode intervals, and also to mechanically ablate and remove at least a portion of any remaining non-combustible deposits. More typically, both fuel and oxidant are conveyed through the second heat transfer zone during combustion mode, generally via different channels to prevent pre-ignition upstream of the combustion zone.

In other aspects, other types of pyrolysis reactors can be used. For example, the pyrolysis reactor can correspond to a conventional steam cracking configuration, where the feed passed through pyrolysis tubes that are heated by a steam cracking furnace.

Process gas conducted away from the pyrolysis reactor is compressed in a process gas compressor so that light olefins and other components of the process gas can be separated and recovered in the olefin recovery facility. The process gas compressor is powered by shaft power. At least part of the shaft power is obtained from a turbine operated based on an Allam cycle. These components will now be described in more detail with reference to the following definitions, which shall apply to this description and appended claims.

Definitions

The following terms are defined for this description and appended claims.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, and including mixtures of hydrocarbon compounds (saturated and/or unsaturated), such as mixtures of hydrocarbon compounds having different values of n.

The terms "alkane" and "paraffinic hydrocarbon" mean substantially-saturated compounds containing hydrogen and carbon only, e.g., those containing ≤1% (molar basis) of unsaturated carbon atoms. The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic ring.

The terms "regenerator", "recuperator", "regenerative bed", "monolith", "honeycomb", "reactant", "fuel", and "oxidant" have the meanings disclosed in U.S. Pat. No. 7,943,808, which is incorporated by reference herein in its entirety. A "pyrolysis reactor" is a reactor, or combination of reactors or a reactor system for hydrocarbon pyrolysis. The term "pyrolysis stage" means at least one pyrolysis reactor, and optionally including means for conducting one or more feeds thereto and/or one or more products away therefrom. A "region" or "zone" is a location, e.g., a specific volume, within a reactor, a location between two reactors and/or the combination of different locations in one or more reactors. A "pyrolysis region" is a location where pyrolysis is carried out, e.g., in a location which contains or is proximate to components, such as at least one thermal mass, which provides heat for the pyrolysis. A reactor or reaction stage can encompass one or more reaction regions. More than one reaction can be carried out in a reactor, stage, or region.

A pyrolysis region can include components having conduits, channels, and passages. The term "conduit" refers to means for conducting a composition from one location to another. The term encompasses (i) elementary conducting means, such as a pipe or tube, and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, with the channel having a plurality of passages or sets of passages.

The term "bulk gas temperature" means the temperature of a bulk gas steam as measured by a device (such as a thermocouple) that is in contact with the bulk gas but not in contact with a solid thermal mass. For example, if the gas is traveling through an internal channel of length $L_c$ of a thermal mass in the pyrolysis zone of a thermal pyrolysis reactor, the bulk gas temperature at a location along $L_c$ is the average temperature (arithmetic mean) over the channel's cross sectional area at that location. The peak gas temperature is the greatest cross-sectional-averaged bulk gas temperature achieved along a flow path. One skilled in the art will appreciate that a gas temperature immediately proximate to a solid thermal mass, such as a partition between passages within a thermal mass at any particular location may exceed the bulk gas temperature, and may, in some infinitesimal layer, actually approach the solid's temperature. The average bulk gas temperature "$T_{av}$" over a region of the reactor, e.g., of the pyrolysis zone, is obtained using the formula:

$$T_{av} = \left[ \frac{1}{b-a} \times \int_a^b T(x)dx \right].$$

Parameters a and b are the boundaries of an interval (distance) along the long axis of the reactor. For example, referring to FIG. 2, parameter "a" can be the position of aperture 5 and parameter "b" can be the position of aperture 9. T(x) is a function representing the variation of bulk gas temperature over the interval of from a to b. When T(x) is a bulk gas temperature profile of a pyrolysis zone, e.g., the pyrolysis zones indicated (at the start of $t_P$) by the shaded regions in FIG. 3, parameters a and b are the locations where the bulk gas temperature profile intersects the line $T_{MIN}$, which corresponds to the minimum temperature at which feed conversion is ≥10% under the selected pyrolysis conditions and feed. Since the bulk gas temperature profile typically changes during the pyrolysis time interval $t_P$, as shown in FIG. 3, $T_{av}$ will typically decrease during $t_P$. The portion of the profile having a temperature ≥$T_{MIN}$ can be continuous, but this is not required. For example, when a profile that intersects $T_{MIN}$ at more than two locations in the pyrolysis zone (e.g., a, b) and touches $T_{MIN}$ at a location c (not shown, but between a and b), additional integrations are carried out, e.g.:

$$Tav = \frac{1}{b-a} \int_a^b T(x)dx + \frac{1}{c-b} \int_b^c T(x)dx.$$

When the portion of the profile that is $\geq T_{MIN}$ is in the form of discrete segments, the integrations are performed over each of the segments.

The term "pyrolysis" means an on-average endothermic reaction for converting molecules into (i) atoms and/or (ii) molecules of lesser molecular weight, and optionally (iii) molecules of greater molecular weight, e.g., processes for converting ethane and/or propane to molecular hydrogen and unsaturates such as ethylene, propylene and acetylene.

A hydrocarbon feed is subjected to "thermal pyrolysis" when <50.0% of the heat utilized by the pyrolysis is provided by exothermically reacting the hydrocarbon feed, e.g., with an oxidant, e.g., ≤25%, such as ≤10%, or ≤1%. The "severity threshold temperature" for pyrolysis is the lowest bulk gas temperature at which acetylene selectivity is at least 10% for a residence time ≤0.1 second. High-severity pyrolysis conditions are those carried out at a peak gas temperature that is greater than or equal to the severity threshold temperature. Low-severity pyrolysis conditions are those carried out at a peak gas temperature that is less than the severity threshold temperature, i.e., conditions under which substantially no hydrocarbon pyrolysis is carried out at a pyrolysis gas temperature that exceeds the severity threshold temperature. High-severity conditions include those which exhibit (i) a methane selectivity ≥5 wt. % and/or (ii) a propylene selectivity at a temperature ≥1000° C. of ≤0.6 wt. %. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor.

The term "Periodic Table" means the Periodic Chart of the Elements appearing on the inside cover of The Merck Index, Twelfth Edition, Merck & Co., Inc., 1996. "Steam Tables" can be found in M. D. Koretsky, "Engineering and Chemical Thermodynamics", John Wiley & Sons, 2004. When a temperature is indicated, the units "K" indicate degrees Kelvin, the SI unit of temperature.

Power Plant

In various aspects, the process gas compressor for pyrolysis reactor used for production of ethylene is powered by a power plant that operates based on the Allam cycle. The power plant produces shaft power for powering the process gas compressor. The power plant can correspond to a fuel-fired turbine, where supercritical $CO_2$ is used as the working fluid. This process uses a high-pressure $CO_2$ loop to transfer power without the inefficiencies of the phase envelope encountered in steam cycle power generation. In some aspects, natural gas and substantially pure oxygen are combusted to heat a stream of mostly $CO_2$ to turbine inlet conditions, then a turbine expands this gas to provide shaft power for a power generator. Then, turbine effluent is interchanged with combustor feed to recover energy. Next, water from the combustion process is removed and the stream is compressed and pumped to turbine inlet pressure, where fresh $CO_2$ from combustion can be removed into a pipeline. Using this process, improved efficiency can be gained, approaching 55-60%, without stack emissions of any kind, and without atmospheric $CO_2$ emissions. It is noted that other types of fuel streams can be combusted. For example, a tail gas stream produced after separating various components from the process gas can be used as at least part of the fuel stream.

The tail gas recovered from the process gas can consist essentially of methane and optionally hydrogen at various concentrations. The tail gas stream from a large industrial steam cracker receiving feeds such as ethane can be quite large. In an embodiment of the processes of this disclosure, a portion, and preferably a majority, and preferably the entirety, of the tail gas is combusted in the Allam cycle to produce power, including shaft power and optionally electrical power via coupled electricity generator(s). The shaft power can be advantageously used to drive one or more of the equipment in the olefins production plant, e.g.: a) to a process gas compressor to compress the process gas, b) to a refrigeration compressor to cool the compressed process gas, c) to a refrigeration compressor to cool the decompressed working fluid in a cooling step from the series of cooling and compressing steps, or d) a combination of two or more of a), b) and c). Compared to using power sourced from external fuel such as a natural gas stream, or electrical power transmitted from outside of the olefins production plant, using the shaft power produced from tail gas combustion in an Allam cycle can improve the energy efficiency of the olefins production plant significantly. Electrical power can be co-generated in the olefins production plant by coupling a portion of the shaft power to one or more electricity generators to suit the electricity demand in the olefins plant, and to transmit to outside of the plant where appropriate and economic. The in-situ generated electrical power, when consumed on-site, does not involve transmission loss otherwise unavoidable if it were transmitted from a remote power plant. An olefins production plant consumes a large quantity of shaft power, which can be met by using a large scale Allam cycle achieving a very high level of economy of scale. In contrast, the power production units disclosed in U.S. Patent Application Publication No. 2017/0058712 A1 are at much smaller in scale and therefore less efficient.

In a conventional Brayton cycle such as one disclosed in U.S. Patent Application Publication No. 2019/0169510 A1, the exhaust gas comprising $CO_2$ and water produced from fuel combustion is typically vented into the atmosphere, resulting in large $CO_2$ emission and loss of water vapor. On the contrary, any water produced in the Allam cycle of the processes of this disclosure can be advantageously reused. For example, at least a portion of a water stream can be (i) fed into the pyrolysing step to mix with the hydrocarbon-containing feed; (ii) heated to generate steam; (iii) used as an indirect cooling medium; (iv) used as a quenching medium; and (iv) fed into a hydrocarbon-containing stream as a diluent. An olefins production plant utilizes a lot of water for cooling and as process diluent. The Allam cycle used in the processes of this disclosure in an olefins production plant can produce very large quantity (e.g., 1500 kilotons per year for a state-of-art olefins production plant) of water due to the amount of fuel combusted. By reusing the water stream produced from the Allam cycle, demand of externally-sourced water is reduced in the plant, further increasing the plant efficiency, reducing the plant carbon footprint, and improving the environmental friendliness thereof.

An olefin product produced from an olefins production plant can be an ethylene stream. The ethylene product can find many industrial uses. For example, the ethylene stream can be supplied via a pipeline to a nearby polyethylene production plant where it is converted into polyethylene. In another embodiment, a portion of the ethylene product can be converted into glycol products including but not limited to monoethylene glycol ("MEG"), which, in turn, can be used in vehicle antifreeze and in processes for making polyester polymers. In a particularly advantageous process, ethylene can be first oxidized by oxygen to produce an oxidized mixture comprising ethylene oxide, which can subsequently hydrolyze to make MEG, or contact $CO_2$ to produce ethylene carbonate followed by hydrolysis to make MEG:

$$Ethylene + O_2 \rightarrow Ethylene\ oxide \quad (1)$$

$$Ethylene\ oxide + H_2O \rightarrow MEG \quad (2)$$

$$Ethylene\ oxide + CO_2 \rightarrow Ethylene\ carbonate\ (C_3H_4O_3) \quad (3)$$

$$Ethylene\ carbonate + H_2O \rightarrow MEG + CO_2 \quad (4)$$

The oxygen consumed in reaction (1) above can be supplied by an air separation facility which also supplies the oxygen-containing stream required for combusting the fuel such as the tail gas in the Allam cycle. By using a common air separation facility for two processes, which is costly, one can achieve an economy of scale otherwise not possible, resulting in a high energy efficiency and cost effectiveness among all involved plants.

The $CO_2$-containing stream and/or the compressed $CO_2$ stream produced from the Allam cycle in the processes of this disclosure can be put into advantaged use in various embodiments. For example, a portion of the $CO_2$ produced in the Allam cycle can be supplied to reaction (4) in the preceding paragraph, enabling the efficient production of MEG from the ethylene produced from the ethylene production plant. In another example, a portion of the compressed $CO_2$ stream can be used to extract a hydrocarbon source material, which, in turn, can be used to derive at least a portion of the hydrocarbon-containing feed subjected to pyrolysis to make the olefins products. Such hydrocarbon source material can be, e.g., crude oil, shale oil, shale gas, natural gas, and the like, stored in underground geological formations. From the extracted crude oil, shale oil, shale gas, and/or natural gas, one can derive a suitable feed, e.g., a natural gas stream, an ethane stream, and the like, as feed to the steam cracker in an olefins production plant. The integration of the Allam cycle, olefins production, and hydrocarbon extraction in such manner can greatly facilitate the overall production processes, and substantially increase the overall energy efficiency. Any surplus $CO_2$ produced from the Allam cycle can be conveniently injected into underground storages for sequestration, which are frequently available at hydrocarbon extraction sites. Alternatively or additionally, a portion of the compressed $CO_2$ stream can be conveniently supplied via a pipeline to other locations for sale, storage, or use. Overall, the olefins production processes of this disclosure can leave a very small $CO_2$ footprint, in stark contrast to a conventional process which can produce large quantity of $CO_2$.

By combusting the large quantity tail gas produced in the olefins production plant in the Allam cycle in the processes of this disclosure, one therefore can conveniently dispose of a relatively low value fuel stream, produce large and flexible quantities of shaft power and/or electrical power as needed by the olefins production plant, supply a large quantity of process water otherwise required from external source to the olefins production plant, supply oxygen to adjacent processes such as MEG production processes at higher economy of scale, and facilitate hydrocarbon extraction using the $CO_2$ stream, all with a minimized $CO_2$ emission and water emission. The total benefit of the processes of this disclosure can be enormous.

To drive multiple compressors, the $CO_2$ loop can be split among compressors to be powered. In such an aspect, combustors can be located next to the turbine inlets to minimize hot piping and allow individual isolation/maintenance. Each compressor can be coupled with the $CO_2$ loop turbines to drive the compressors without boiler emissions from steam turbine driver, gas turbine combustion emissions from gas turbine driver, or outside-of-fence power generation emissions from incremental grid electric power for an electric motor driver.

In addition, instead of using only natural gas for combustion as may be practiced in the power industry, ethylene unit tail gas can be used for combustion, with the consequence of reduced $CO_2$ generation and increased water removal. Alternately, natural gas may be used with the Allam cycle for compression power while hydrogen-rich tail gas is supplied to traditional combustion sources like steam cracking furnaces or boilers to reduce net $CO_2$ emissions.

To supply power in this fashion, a compressor is added to the ethylene plant to compress $CO_2$ in the $CO_2$ loop up to a pressure where the supercritical fluid exhibits reduced, minimized, or no compressibility upon increased pressure. Additionally or alternately, additional compression can be used to compress separated oxygen and natural gas to a target pressure prior to combustion, such as a pressure of 200 bar or more, or 250 bar or more, or 300 bar or more, such as up to 600 bar or possibly still higher. After combustion, the pressurized, heated working fluid is used to drive a turbine. This can reduce the pressure of the depressurized working fluid to a pressure of 70 bar or less, or 60 bar or less, or 50 bar or less, such as down to 20 bar or possibly still lower. This equipment can use excess power from the turbine power step to drive these supporting steps. Thus, even though the ethylene plant requires modification in order to be integrated with the Allam cycle, this modification does not require a further, separate power source.

Figure 6:
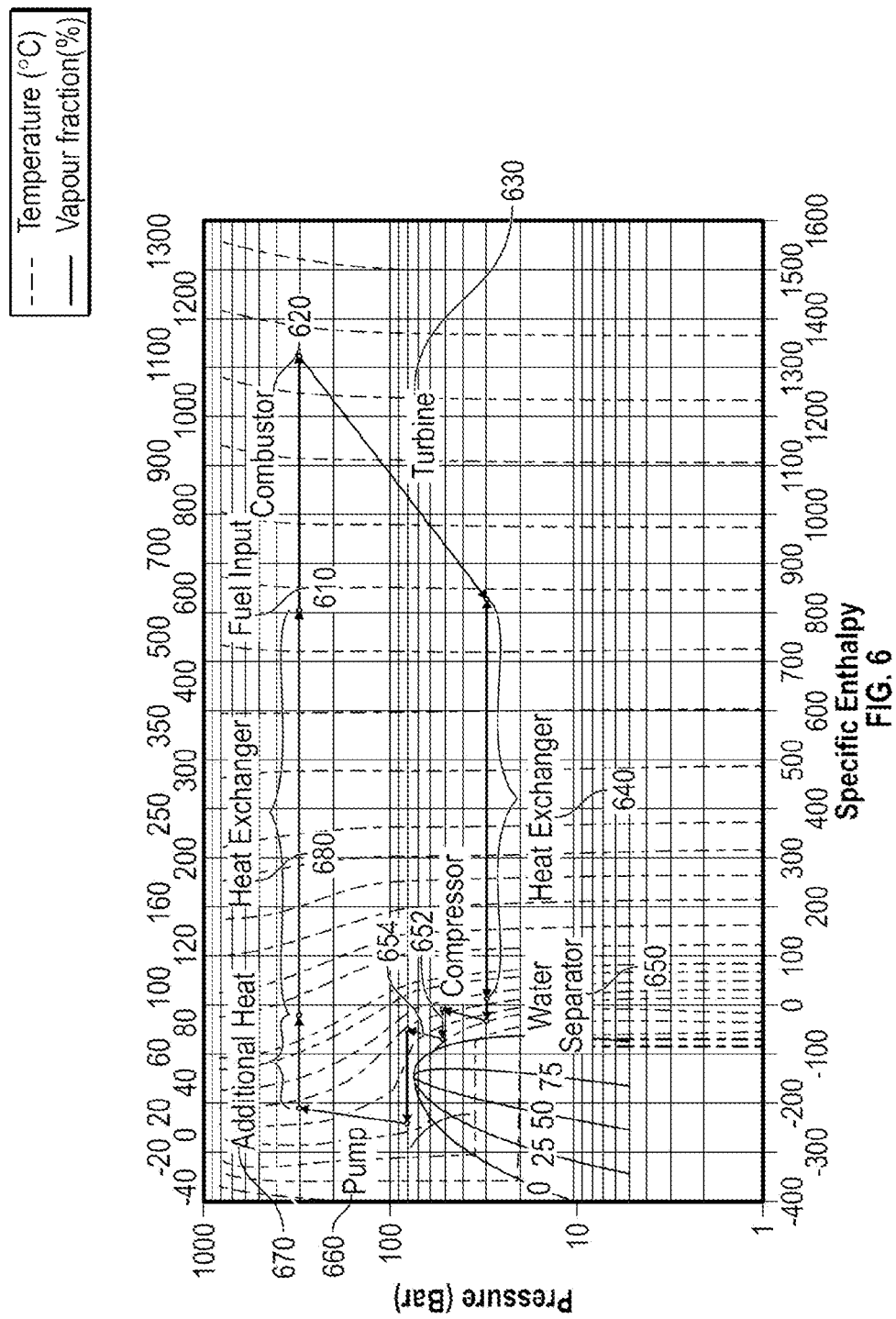
FIG. 6 shows a Mollier diagram for operating a single turbine and a single combustor based on an Allam cycle.

FIG. 6 shows an example of a Mollier diagram (pressure versus enthalpy plot) for a single combustor and a turbine operating based on an Allam cycle. FIG. 6 also shows lines corresponding to constant temperature curves, as well as the region of phase space where distinct vapor and liquid phases of $CO_2$ can be present due to $CO_2$ not being in a supercritical state.

In FIG. 6, the Allam cycle is illustrated based on how various processes within the cycle result in pressure and/or enthalpy changes for the working fluid. The cycle begins with addition of fuel input 610 to the working fluid prior to passing the fuel and working fluid into the combustor. The fuel is combusted 620, which results in an increase in enthalpy at relatively constant pressure. This high pressure, high enthalpy working fluid is then used to power a turbine 630. Powering the turbine 630 results in a reduction in both pressure and enthalpy for the working fluid. The depressurized working fluid is then heat exchanged 640 with the high pressure working fluid 680 that the fuel input 610 is combined with. The heat exchange reduces the enthalpy of the low pressure working fluid while increasing the enthalpy of the high pressure working fluid.

After heat exchange, water is removed 650 from the working fluid. The water removal is performed by cooling the working fluid to condense the water. However, such cooling has the potential to also place the working fluid in a region of phase space where the $CO_2$ in the working fluid would no longer be supercritical. To avoid this, as shown in FIG. 6, the water removal 650 is performed in a series of alternating cooling steps 652 and compression steps 654. This allows the $CO_2$ in the working fluid to remain (substantially) in a supercritical state during the water removal process, so that no phase changes occur in the working fluid. After water removal 650, the remaining working fluid substantially corresponds to $CO_2$. The $CO_2$ working fluid is then further compressed 660 to return the working fluid to the desired temperature for the combustor 620. After pressurization 660, the working fluid is then heated 670 and heat exchanged 680 in preparation for the combustor.

It is noted that the number of compression and cooling steps used during the alternating series of compression and cooling steps can vary depending on the nature of the fuel for the combustor associated with the turbine. In particular, as the amount of $H_2$ in the fuel to the combustor is increased, the likelihood of $CO_2$ condensation can modestly decrease. Thus, using a fuel such as tail gas from the pyrolysis process can potentially reduce the number of separate compression and cooling steps are needed for removing water while avoiding a phase change for the $CO_2$ in the working fluid. In addition, use of a fuel such as tail gas from the pyrolysis process can potentially reduce air separation requirements as less oxygen is required for combustion of the higher $H_2$ content fuel.

Figure 5:
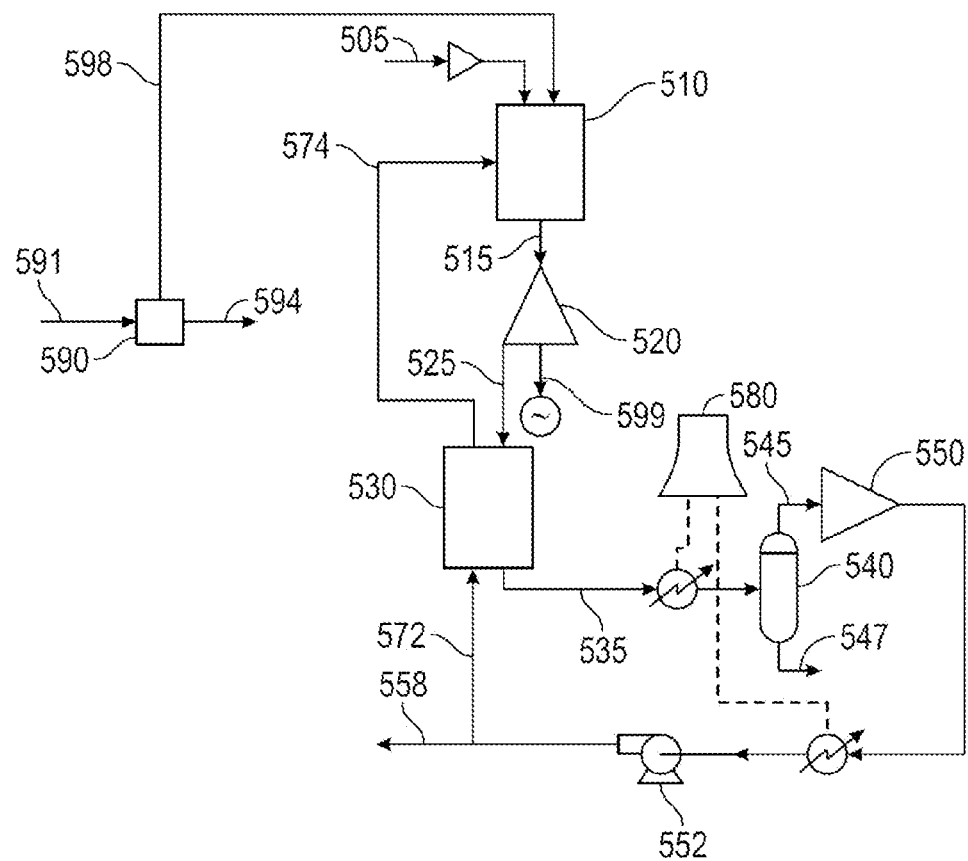
FIG. 5 shows an example of a power generation system suitable for operating a turbine based on an Allam cycle.

FIG. 5 shows an example of a process flow for operating a turbine based on an Allam cycle, such as the cycle shown in FIG. 6. In FIG. 5, air 591 is passed into an air separation unit 590. This produces a high purity oxygen stream 598 and remainder stream 594 corresponding to nitrogen and the other components of air 591 that are not included in the high purity oxygen stream 598. The high purity oxygen stream 598 can include 90 vol. % or more of $O_2$, or 95 vol. % or more, such as up to having substantially all of oxygen stream 598 correspond to $O_2$ (less than 1 vol. % of other components). By forming a high purity oxygen stream 598, a subsequent combustion process can be performed where a reduced or minimized amount of $N_2$ or other diluents are present.

The oxygen stream 598 is passed into a combustor 510. A fuel stream 505 is also passed into combustor 510. A combustion reaction can be performed in combustor 510 to generate heat, $CO_2$, and $H_2O$. An additional recycle flow of $CO_2$ 574 can also be passed into combustor 510 as a working fluid to absorb additional heat from the combustion reaction. The combined gas phase products from the combustion reaction and the additional recycle flow 574 exit the combustor 510 as gas flow 515. Because oxygen stream 598 includes a reduced or minimized amount of components other than $O_2$, the gas flow 515 can correspond to 80 vol. % or more of $CO_2$ and $H_2O$, or 90 vol. % or more, or 95 vol. % or more. The gas flow 515 is then used to drive turbine 520, which provides shaft power 599 for one or more process gas compressors. This results in a reduced pressure gas flow 525.

After powering turbine 520, the reduced pressure gas flow 525 is passed into a heat exchanger 530 to transfer heat to the additional recycle flow 574. The heat exchanged gas flow 535 is then further cooled by heat exchange with fluid from cooler 580. After the further cooling, the heat exchanged gas flow 535 is then passed into separator 540 to separate out water 547. The remaining portion 545 of the gas flow can correspond to 90 vol. % or more $CO_2$, or 95 vol. % or more $CO_2$, or 97 vol. % or more $CO_2$. The remaining portion 545 of the gas flow is then cooled further prior to additional compression and/or pumping, such as by using compression stage 550 and/or pump 552, to form a high-pressure $CO_2$-containing gas flow 558. Optionally, the cooling prior to compression can be further assisted by heat exchange with an interstage cooling stream, such as an interstage cooling stream (not shown) from air separation unit 590. A portion 572 of the high-pressure $CO_2$ gas flow is passed into heat exchanger to form additional recycle flow 574.

The composition of the working fluid can vary, depending on the location in the cycle where the working fluid is sampled. After combustion and prior to removal of water, the working fluid can include $CO_2$, CO, $H_2O$, and optionally one or more components that are present due to the fuel containing compounds other than hydrogen and hydrocarbons and/or due to use of an oxygen-containing stream that contains compounds other than oxygen. Optionally but preferably, the oxygen-containing stream can include 90 vol. % or more of $O_2$, or 95 vol. % or more, or 97 vol. % or more, such as having an oxygen-containing stream that is substantially composed of $O_2$ (less than 0.1 vol. % of components different from $O_2$). Optionally but preferably, the fuel used for combustion can include 90 vol. % or more of hydrogen, hydrocarbons, CO, $CO_2$, and $H_2O$, or 95 vol. % or more, or 97 vol. % or more, such as up to containing 0.1 vol. % or less of other components. Suitable fuels include those specified for pyrolysis reactor regeneration, e.g., a fuel having a heating value $\geq 1 \times 10^6$ J/kg. For example, the fuel can comprise one or more of natural gas, gaseous hydrocarbon in the natural gas, gaseous hydrocarbon separated from the natural gas and/or derived from the natural gas, gaseous hydrocarbon separated from the natural gas condensate and/or derived from the natural gas condensate, gaseous hydrocarbon separated from the crude oil and/or derived from the crude oil, molecular hydrogen, carbon monoxide, and mixtures thereof. Additionally or alternately, a tail gas stream generated from the ethylene plant can be used as at least a portion of the fuel.

After water separation and prior to addition of more fuel, the working fluid can include less than 1.0 vol. % water, or less than 0.1 vol. % water. Additionally or alternately, the working fluid after water separation and prior to addition of more fuel can include 90 vol. % or more of $CO_2$, or 95 vol. % or more, or 97 vol. % or more, such as up being substantially composed of $CO_2$ (less than 1.0 vol. % of components different from $CO_2$, or less than 0.1 vol. %.)

The shaft power generated by the turbine can potentially be used to power a variety of components within the process train for processing a pyrolysis effluent. In some aspects, the power from the turbine can be used to drive a process gas compressor. Another option can be to use at least a portion of the shaft power from the turbine can be used to drive a compressor that is part of a refrigeration unit for cooling one or more portions of the pyrolysis effluent. Still another option can be to use the shaft power to drive a compressor involved in the compression and cooling steps used for removing water from the working fluid while maintaining the $CO_2$ in a substantially supercritical state. It is noted that compressors can be used for both compression and refrigeration during the compression and cooling steps. In some aspects, portions of shaft power from a turbine operating based on the Allam cycle can be used to power a plurality of the above types of compression and/or refrigeration processes. In still other aspects, any other convenient integrated use of shaft power can be implemented.

Figure 4:
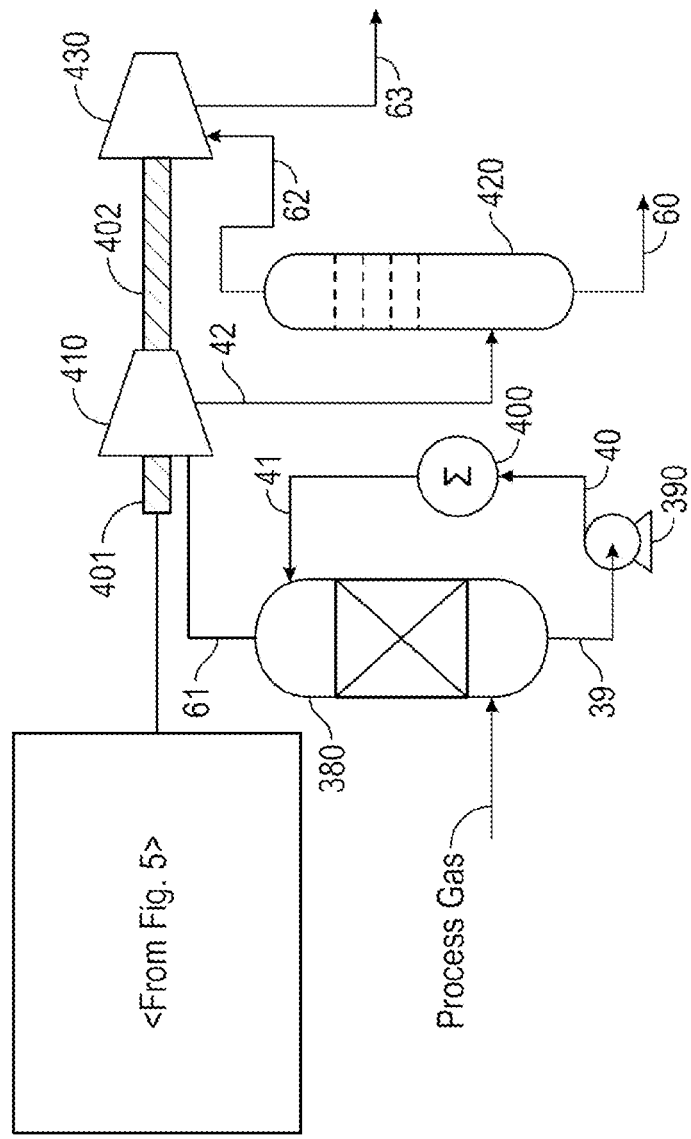
FIG. 4 schematically shows certain aspects of the invention in which a process gas produced derived from hydrocarbon pyrolysis product is compressed in a process gas compressor.

FIG. 4 shows an example of how the shaft power 599 provided by turbine 520 in FIG. 5 can be utilized to power a process gas compressor. An example of a suitable power plant is shown schematically in FIG. 4. In FIG. 4, process gas (e.g., from line 49 of FIGS. 1 and 2) is conducted to cooling stage 380 (typically a quench tower or combined quench tower-primary fractionator) to produce a cooled process gas, which is conducted away via line 61. Water is a typical quench medium, which can be recovered via line 39, pressurized in pump 390, conducted to cooler 400 via line 40, and returned to the cooling stage via line 41. Cooled process gas is initially pressurized in compressor stages 410, which typically include at least three stages of increasing compression and inter-stage cooling. Pressurized process gas from the compressor stages 410 is conducted via line 42 to process gas upgrading equipment, typically caustic and/or amine treatment, shown schematically as tower 420. Spent treatment medium (e.g., spent caustic) is conducted away via line 60. Upgraded process gas is conducted via line 62 to second compression stages 430 for further pressurization. Typically, stages 410 and 430 are joined by rotating shaft 402, which may be joined to rotating shaft 401 for powering these stages. Shaft 402 obtains at least a portion of its shaft power from turbine 520 (as shown in FIG. 5). This can be accomplished by (i) a direct transfer of rotational energy, e.g., via a rotational power transmission; (ii) an indirect transfer, e.g., by powering an electric generator with power 599 from turbine 520, driving an electric motor with at least a portion of the electric power produced by the generator, and using the motor to power shaft 401; and (iii) a combination of direct and indirect power transmission. Compressed process gas is conducted away via line 63 for storage and/or further processing, e.g., drying, acetylene conversion, and recovery of products such as ethylene.

Representative Regenerative Thermal Pyrolysis Reactors

Regenerative pyrolysis reactors are an example of a suitable reactor for producing ethylene from a hydrocarbon feed. Regenerative pyrolysis reactors typically comprise an internal volume having at least one region. A regenerable thermal mass having at least one internal channel is positioned in this region. A reactor temperature profile is established sufficient for carrying out the pyrolysis, e.g., by heating the thermal mass, and a flow of the hydrocarbon-containing feed is established through the channel Heat is transferred from the thermal mass to the hydrocarbon feed, which increases the hydrocarbon feed's temperature and results in thermal pyrolysis of at least a portion of the feed, e.g., pyrolysis carried out in the substantial absence of oxidant. The pyrolysis produces a pyrolysis product typically comprising molecular hydrogen, methane, acetylene, ethylene, and $C_{3+}$ hydrocarbon, where the $C_{3+}$ hydrocarbon includes coke and coke precursors. At least a portion of the coke typically remains in the passages of the thermal mass, and the remainder of the pyrolysis product is typically conducted away from the reactor as the process gas. Since the pyrolysis is endothermic, pyrolysis mode operation will eventually cool the thermal mass, e.g., to a temperature at which the pyrolysis cannot be carried out efficiently. The ability to efficiently carry out pyrolysis reactions is restored by regenerating the reactor during regeneration mode.

Figure 2:
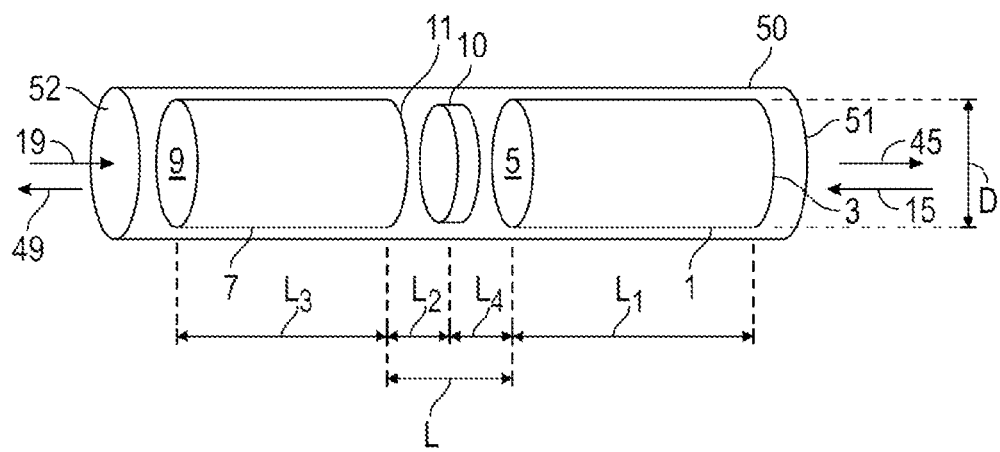
FIG. 2 schematically shows forms of a representative reverse flow thermal pyrolysis reactor.
Figure 3:
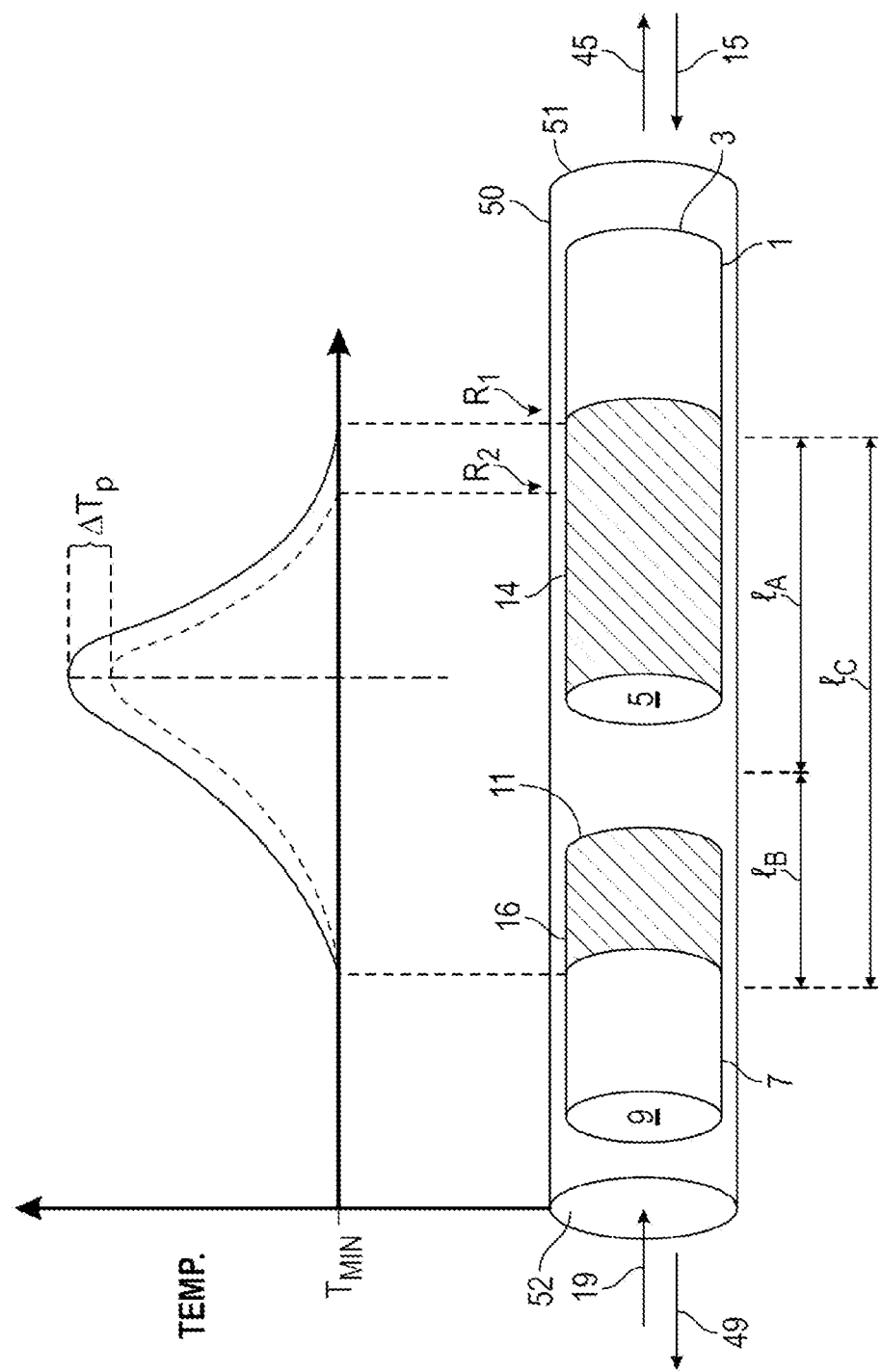
FIG. 3 schematically show representative bulk gas temperature profiles at the start (solid lines) and end (dashed lines) of pyrolysis mode for the reactor of FIG. 2.

Thermal characteristics of reactor 50 of FIGS. 2 and 3 are substantially congruent with those described in connection with conceptual reactor 101 of FIG. 1. Reactor 50 is in the form of an elongated tubular vessel having an internal volume which includes at least one heat transfer zone and at least one pyrolysis zone. The reactor vessel's cross sectional shape and/or cross sectional area can be substantially uniform over the length of the reactor, but this is not required. For example, one or more segments of the reactor vessel's length can have a circular, elliptical, or polygonal cross section. Reactor 50 has opposed first and second openings 51 and 52 which are in fluidic communication with the internal volume and are located at terminal ends of the reactor vessel. The first and second openings are separated by reactor length $L_R$. The reactor also includes at least one thermal mass 1 located in a first region of the internal volume. The thermal mass has at least one internal channel that typically has a length substantially equal to $L_1$. The thermal mass also has a first aperture 3 and a second aperture 5 in fluidic communication with the channel. The first and second apertures are separated by a flow-path through the channel Typically the flow path has a length substantially equal to $L_1$. The first aperture is typically located adjacent to the first opening.

During pyrolysis mode, a forward flow of hydrocarbon-containing feed is established into the channel toward the second aperture by introducing the feed through the first opening 51 via line 15 and through the first aperture 3. Pyrolysis mode is operated during a time interval $t_P$ which starts at a first time $t_1$ and ends at a second time $t_2$. The feed is heated by a transfer of heat from at least a segment of the first thermal mass 1 (conceptually the first heat transfer zone). Typically, a first segment of the first thermal mass 1 is located in the first heat transfer zone (the un-shaded segment of first thermal mass 1 as shown in FIG. 3), with a second segment being located in the pyrolysis zone (the shaded segment). This heat transfer sufficiently heats the feed so that it undergoes thermal pyrolysis in the reactor's internal volume, e.g., proximate to thermal mass 1, which produces a flow of a pyrolysis product comprising molecular hydrogen and $C_{2+}$ olefin. The pyrolysis conditions include a gas temperature profile within the reactor at $t_1$ which exhibits a peak gas temperature $T_p$ and an average gas temperature $T_{av}$ that is $<T_p$. $T_p$ is typically in the range of from 800° C. to 1400° C. Typically, the bulk gas temperature profile at the start of pyrolysis mode (solid curve) continuously varies over the length of the pyrolysis zone. The pyrolysis is on average endothermic, so carrying out the pyrolysis cools the reactor during $t_P$, resulting in a decrease in $T_p$ and a second bulk gas temperature profile (dashed curve) at $t_2$. The flow of the pyrolysis product is conducted into the second region of the internal volume via the second aperture 5, and the process gas is conducted away from the reactor via the second opening 52 and line 49. Optionally, a second thermal mass 7 is positioned in the reactor's internal volume as shown in FIGS. 2 and 3. The pyrolysis product is cooled in the reactor's internal volume by a transfer of heat from the pyrolysis product to at least a segment of second thermal mass 7 (conceptually, the second heat transfer zone). Typically, a first segment of the second thermal mass 7 is located in the second heat transfer zone (the un-shaded segment of second thermal mass 7 as shown in FIG. 3), and a second segment is located in the pyrolysis zone (the shaded segment). Following pyrolysis mode (e.g., after $t_2$), the reactor is regenerated by operating in regeneration mode for a regeneration time interval $t_R$ that is of sufficient duration to at least partially restore the reactor to conditions under which additional pyrolysis can be carried out.

In certain aspects (not shown), regeneration includes combusting at least a portion of a fuel-oxidant heating mixture during $t_R$ in a location other than within the internal volume of reactor 50. For example, fuel combustion can be carried out at a location external to reactor 50, with the combustion products, unreacted oxidant, and optionally unreacted fuel being conveyed to the vicinity of the pyrolysis zone for (i) heating the pyrolysis zone to provide a desired temperature profile for efficiently carrying out the pyrolysis and (ii) removing at least a portion of any deposits remaining in the reactor at the start of regeneration mode. In aspects where optional second thermal mass 7 is present in reactor 50, as shown in FIGS. 2 and 3, regeneration mode includes conveying a reverse-flow of heating mixture 19 comprising fuel and oxidant through opening 52, through aperture 9 of thermal mass 7, and out of aperture 11 toward a region of the reactor's internal volume located between the first and second thermal masses (which region conceptually corresponds to the combustion zone). Typically, the fuel and oxidant are conveyed separately through different channels of second thermal mass 7 from aperture 9 toward aperture 11, and are mixed and distributed by mixer-distributor 10 to form the heating mixture downstream (with respect to fuel/oxidant flow) of thermal mass 7. Typically fuel and oxidant are heated by a transfer of heat from at least a segment of thermal mass 7 (conceptually, the second heat transfer zone) as the fuel and oxidant flow through channels of thermal mass 7. Combustion of the fuel and oxidant produces a combustion effluent in the region of the reactor's internal volume between thermal masses 7 and 1 (conceptually, the combustion zone). Combustion effluent, any un-combusted oxidant, and any un-combusted fuel enter aperture 5. An aggregated combustion effluent 45 is conducted out of aperture 3 and away from the reactor via opening 51. The aggregate combustion effluent typically comprises combustion effluent produced in a region of the internal volume located between apertures 11 and 5; additional combustion effluent, typically from deposits-removal in passages of thermal mass 1; and any unreacted fuel and/or any unreacted oxidant. Heat is transferred from the combustion effluent to at least a segment of the first thermal mass (conceptually corresponding to the first heat transfer zone).

Combustion can be carried out in a region within the internal volume of reactor 50, e.g., an open volume having a length L and substantially constant circular cross section of diameter D and cross sectional area A (not shown). As may be appreciated, an open volume having an appropriate L: A ratio will provide at least some mixing and distribution during regeneration mode without creating too great a pressure drop during pyrolysis mode. More typically, since it provides improved mixing and distribution and allows a lesser overall length for the combustion zone, the combustion zone includes at least one mixer-distributor apparatus 10. When used, mixer-distributor 10 can be centered in the region between apertures 11 and 5, e.g., with $L_2$ being substantially equal to $L_4$. The sum of lengths $L_1$, L, and $L_3$ is typically ≥90% of the total length of reactor 50 ($L_R$), e.g., as measured between openings 51 and 52. Since it is desirable to direct fuel and oxidant flows into appropriate passages of thermal mass 7 during regeneration mode and to direct pyrolysis feed flow into appropriate passages of thermal mass 1 during pyrolysis mode, it can be desirable to limit the internal volume between aperture 9 and opening 52 and between aperture 3 and opening 51 to that needed for convenient reactor assembly and to prevent component interference as might otherwise occur from thermal expansion during use. For, example, the distance along the flow path between aperture 9 and opening 52 is typically ≤0.1 $L_R$, such as ≤0.01 $L_R$, or ≤0.01 $L_R$. Likewise, the distance along the flow path between aperture 3 and opening 51 is typically ≤0.1 $L_R$, such as ≤0.01 $L_R$, or ≤0.01 $L_R$. The pyrolysis zone, which generally encompasses all of region L, a segment of $L_1$, and a segment of $L_3$, is typically ≥10% of the total length of reactor 50, e.g., ≥15%, or ≥20%. It is also typical for the pyrolysis zone to encompass ≤80% of the total length of reactor 50, e.g., to leave sufficient internal volume of thermal mass 1 for pre-heating the pyrolysis feed and sufficient internal volume of thermal mass 7 for pyrolysis product quenching, such as, ≤60%, or ≤40%. In certain aspects, the pyrolysis zone has a length in the range of from 10% to 60% of the total length of the reactor, e.g., in the range of from 20% to 40%. The combustion zone's length L is typically ≤50% of that of the length of the pyrolysis zone, e.g., ≤40%, such as ≤30%, or ≤20%.

Values for L, $L_1$, $L_2$, $L_3$, $L_4$, and D generally depend on the pyrolysis feed used and the rate at which it is conducted into the reactor, the fuel and oxidant compositions, and the rate at which these are conducted into the reactor, etc. Although larger and small reactors are within the scope of the invention, (i) D is typically ≥1 cm, e.g., in the range of from about 1 cm to 10 m, such as 0.1 m to 7.5 m, (ii) $L_R$ is typically ≥1 cm, e.g., in the range of from about 1 cm to 20 m, such as 0.1 m to 7.5 m, (iii) L is typically ≤25% of $L_R$, e.g., ≤10%, (iv) $L_1$ is typically ≥35% of $L_R$ e.g., ≥45%, (v) $L_3$ is typically ≥35% of $L_R$, e.g., ≥45%, $L_3$ being optionally of substantially the same size and shape as $L_1$, and (vi) $L_2$ is typically within about +/−25% of $L_4$, e.g., +/−10%, such as +/−5%.

The mixer-distributor is typically configured to (i) mix the fuel and a portion of the oxidant during regeneration mode for efficient combustion, (ii) increase distribution uniformity over the first heat transfer zone's internal cross sectional area of the combustion products, unreacted oxidant, and optionally unreacted fuel, and (iii) lessen undesirable pressure-drop effects during pyrolysis mode. The mixer-distributor, which can have the form of a relatively thin member (e.g., a plate) having one or more orifices effective for carrying out the mixing and distribution during regeneration mode. Generally, the orifices have sufficient cross sectional area to prevent an undesirably large pressure drop across the reactor during pyrolysis mode. Conventional mixer-distributors can be used, such as those described in U.S. Patent Application Publication No. 2013-0157205 A1 and U.S. Pat. No. 7,815,873 (incorporated by reference herein in their entireties), but the invention is not limited thereto. Optionally, combustion is carried out in the presence of at least one selective combustion catalyst, e.g., one or more of those described in U.S. Pat. No. 8,754,276, but the invention is not limited thereto. When used, a fixed bed of the selective combustion catalyst can be included as a component of the mixer-distributor, e.g., with one or more of the mixer-distributor's plate members serving as a catalyst support. In certain aspects, however, such as those where the amount of coke deposits in thermal mass 1 exceed that of thermal mass 7, the combustion zone is shifted downstream (with respect to fuel-oxidant flow) toward thermal mass 1. The amount of shift is typically ≤25% of L, e.g., ≤20%, such as ≤10%.

The combustion zone occupies a region of reactor 50's internal volume during $t_R$ that is within the pyrolysis zone during $t_P$. However, since in the aspects illustrated in FIGS. 2 and 3 regeneration mode is not carried out at the same time as pyrolysis mode, appreciable combustion does not occur in the combustion zone during pyrolysis mode and appreciable pyrolysis does not occur in the pyrolysis zone during regeneration mode. Reactor 50 can be switched from regeneration mode to pyrolysis mode after sufficiently removing any accumulated deposits and achieving the desired reactor temperature profile for pyrolysis.

Typically, the first and second thermal masses comprise bedding or packing material that is effective in storing and transferring heat, such as glass or ceramic beads or spheres, metal beads or spheres, ceramic (e.g., ceramics, which may include alumina, yttria, and zirconia) or honeycomb materials comprising ceramic and/or metal, other forms of tubes comprising ceramic and/or metal, extruded monoliths and the like. The thermal masses and regenerative beds containing thermal masses can be channeled members comprising refractory, e.g., those described in U.S. Pat. Nos. 8,754,276; 9,126,882; 9,346,728; 9,187,382; 7,943,808; 7,846,401; 7,815,873; 9,322,549; and in U.S. Patent Application Publication Nos. 2007-0144940, 2008-300438, 2014-303339, 2014-163287, 2014-163273, 2014-0303416, 2015-166430, 2015-197696, and 2016-176781. These references are incorporated by reference herein in their entireties. Thermal masses 1 and 7 can each have the form of an elongated refractory honeycomb. The honeycomb comprising at least one channel, the channel having a plurality of passages. When the channels and passages are substantially uniform in cross-sectional size and shape, the honeycomb (and segments thereof) has a substantially-constant OFA.

The thermal masses typically have a thermal conductivity in the range of from 0.5 W/m° K to 50 W/m° K, a coefficient of thermal expansion in the range of from $1\times10^{-7}$/° K to $2\times10^{-5}$/° K, an average wetted surface area per unit volume in the range of from 1 $cm^{-1}$ to 100 $cm^{-1}$, and an average wetted surface area per unit volume in the range of from 1 $cm^{-1}$ to 100 $cm^{-1}$. The internal channels of each of the thermal masses typically include a plurality of substantially parallel passages, e.g., at a passage density in the range of from 77000/$m^2$ to $1.3\times10^6$/$m^2$. The thermal mass typically comprises refractory, e.g., one having a heat capacity at 300° K that is ≥0.04 [kJ/(° K kg)] and a density ≥3000 kg/$m^3$. For example, the refractory's specific heat capacity at 300° K can be in the range of from 0.04 [kJ/(° K kg)] to 1.2 [kJ/(° K kg)], and its density can be in the range of from 3000 kg/$m^3$ to 5000 kg/$m^3$.

The choice of refractory composition is not critical, provided it is capable of surviving under pyrolysis mode and regeneration mode conditions for practical run lengths (e.g., months) without significant deterioration or decomposition. Those skilled in the art will appreciate that the compositions of the first and second thermal masses should be selected from among those that substantially maintain integrity (structural and compositions) and functionality during long term exposure to pyrolysis feeds, products, and reaction conditions, e.g., temperatures ≥750° C., such as ≥1200° C., or for increased operating margin ≥1500° C. Conventional refractories can be used, including those comprising at least one oxide of one or more elements selected from Groups 2-14 of the Periodic Table, but the invention is not limited thereto. In particular aspects, the refractory includes oxide of at least one of Al, Si, Mg, Ca, Fe, Mn, Ni, Co, Cr, Ti, Hf, V, Nb, Ta, Mo, W, Sc, La, Yt, Zr, and Ce. The refractory can include non-oxide ceramic.

Representative conditions and feeds for regeneration mode and pyrolysis mode will now be described in more detail. The invention is not limited to these feeds and process conditions, and this description should not be interpreted as foreclosing other feeds and process conditions within the broader scope of the invention.

Regeneration Mode

Regeneration mode is carried out to (i) reheat the pyrolysis zone to establish a temperature profile corresponding to the desired bulk gas temperature profile at the start of a following pyrolysis mode and (ii) remove sufficient deposits from within the reactor's internal volume, which otherwise might lead to an increase in reactor pressure drop. When it is desired to quench the pyrolysis product within the reactor (e.g., to utilize a conceptual second heat transfer zone), regeneration mode optionally includes cooling thermal mass 7 or a segment thereof. Fuel and oxidant contained in the heating mixture combust in the combustion zone during at least part of regeneration mode. A wide range of fuels can be used for combusting with oxidant and regenerate the pyrolysis reactor, including hydrocarbon feed. Generally, the fuel is selected from the group consisting of natural gas, hydrocarbon in the natural gas, hydrocarbon separated from the natural gas and/or derived from the natural gas, natural gas condensate, hydrocarbon in the natural gas condensate, hydrocarbon separated from the natural gas condensate and/or derived from the natural gas condensate, crude oil, hydrocarbon in the crude oil, hydrocarbon separated from the crude oil and or derived from the crude oil, molecular hydrogen, carbon monoxide, and mixtures thereof. Fuel and fuel constituents that do not contain hydrocarbon, e.g., one or more of molecular hydrogen, CO, and synthesis gas are within the scope of the invention. Typically, the fuel is derived from, comprises, consists essentially of, or consists of one or more of molecular hydrogen, CO, methane, methane containing streams, such as coal bed methane, biogas, associated gas, natural gas and mixtures or components thereof, etc. The oxidant is typically one or more of molecular oxygen, ozone, and air, including molecular oxygen in air, oxygen-enriched air, and oxygen-deficient air. Optionally, the fuel and oxidant are the same as those disclosed in U.S. Pat. No. 7,943,808. Feed flow rate depends on factors such as feed composition, reactor volume, pyrolysis conditions, etc. Accordingly, the invention can be carried out over a very wide range of heating mixture flow rates, e.g., at a flow rate ≥0.001 kg/s, such as ≥0.1 kg/s, or ≥10 kg/s, or ≥100 kg/s, or more.

Once a fuel of the desired caloric content (heating value) has been selected, the amounts of fuel and oxidant conducted to the reactor during regeneration mode can be specified in terms of the amount of oxidant needed for combusting the accumulated coke deposits ("$OC_a$") and the amount of oxidant ("$OC_b$") needed for the substantially stoichiometric combustion of the fuel. Typically, the amount of oxidant supplied during regeneration mode is Z●($OC_a$+$OC_b$), wherein Z is generally ≥0.5, e.g., ≥0.8, such as in the range of 0.5 to 5.0, or 0.5 to 3.0, or 0.8 to 3.0. The amounts $OC_a$ and $OC_b$ are on a molar basis. When Z>1.0, the excess oxidant can be utilized, e.g., for one or more of removing at least a portion of any accumulated deposits, moderating the reaction temperature during regeneration mode (as disclosed in U.S. Pat. No. 7,943,808), and conveying heat within the reactor from one zone to another. Generally, a first portion of the oxidant is combusted with the fuel in the combustion zone, and a second portion is combusted with accumulated coke deposits. Typically, the first portion comprises ≥50 wt. % of the total amount of oxidant supplied during regeneration mode, e.g., ≥75 wt. %, or ≥90 wt. %. It is also typical for oxidant flow rate and fuel flow rate to remain substantially constant for the duration of regeneration mode. These flow rates are selected to achieve the desired amount of combustion heating and the desired amount of coke removal during $t_R$. A $t_R$≤30 seconds is typically sufficient for reheating the reactor to achieve the desired bulk gas temperature profile at the start of pyrolysis mode, e.g., ≤25 seconds, such as ≤10 seconds, or ≤1 second, or ≤0.1 second. For example, $t_R$ can be in the range of from 0.01 second to 25 seconds, or 0.05 second to 10 seconds, or 0.05 second to 5 seconds, or 0.05 second to 1 second. The invention is compatible with conventional methods for lessening coke accumulation in thermal masses during regeneration mode, e.g., those described in U.S. Pat. No. 9,187,382, which is incorporated by reference in its entirety.

Other streams can be provided to the reactor during regeneration mode, e.g., one or more diluent streams can be provided, such as by addition of one or more diluents to the heating mixture, such as to the oxidant and/or fuel. Suitable diluents (which can be a diluent mixture) include one or more of, e.g., oxygenate (water, carbon dioxide, etc.), non-combustible species, such as molecular nitrogen ($N_2$), and fuel impurities, such as hydrogen sulfide. For example, the oxidant can comprise 60.0 mole % to 95.0 mole % diluent and 5.0 mole % to 30.0 mole % molecular oxygen per mole of the oxidant, such as when the oxidant is air. Optionally, the oxidant has a mass ratio of diluent to molecular oxygen in the range of 0.5 to 20.0, e.g., in the range of 4.0 to 12.0.

At the end of regeneration mode, the reactor is switched to pyrolysis mode, typically by decreasing or terminating fuel and oxidant flow and commencing or increasing a flow of pyrolysis feed. Representative pyrolysis feeds and process conditions will now be described in more detail. The invention is not limited to these pyrolysis feeds, and this description is not meant to foreclose the use of other pyrolysis feeds.

Pyrolysis Mode

The pyrolysis feed typically comprises $C_{2+}$ hydrocarbon, e.g., ≥1 wt. % of $C_{2+}$ hydrocarbon, such as ≥10 wt. %, or ≥25 wt. %, or ≥50 wt. %, or ≥75 wt. %, or ≥90 wt. %. Typically ≥90 wt. % of the remainder of the pyrolysis feed comprises diluent, e.g., one or more of methane, $CO_2$, water, etc. Suitable pyrolysis feeds include those disclosed in U.S. Patent Application Publication No. 2016-176781, which is incorporated by reference herein in its entirety. Also suitable are feeds which include components such as (i) saturated $C_{4+}$ hydrocarbon and/or (ii) aromatic and/or non-aromatic cores having one or more substantially-saturated $C_{2+}$ side chains. The feed can include a recycled portion of the pyrolysis product. Such recycle, when used, can include, e.g., methane, molecular hydrogen, and $C_{2+}$ hydrocarbon, typically $C_2$ to $C_5$.

The feed hydrocarbon can comprise volatile and non-volatile hydrocarbon, as described in U.S. Patent Application Publication No. 2016-176781. Although the feed hydrocarbon typically includes $C_{2+}$ compounds which contain hydrogen and carbon only, feed hydrocarbon can contain compounds having covalently-bound and/or non-covalently-bound heteroatoms. When present in the feed hydrocarbon, the amount of such heteroatom-containing hydrocarbon compounds is typically ≤10 wt. % based on the weight of the feed's hydrocarbon. Feed hydrocarbon that is substantially-free of non-aliphatic hydrocarbon is within the scope of the invention, as is feed hydrocarbon that is substantially free of aromatic hydrocarbon and/or substantially free of olefinic hydrocarbon, particularly $C_2$-$C_5$ olefin. Substantially-free in this context means <1 wt. % based on the weight of the feed hydrocarbon, such as ≤0.1 wt. %, or ≤0.01 wt. %, or ≤0.001 wt. %.

The feed hydrocarbon can be obtained from one or more sources of hydrocarbon, e.g., from natural hydrocarbon sources including those associated with producing petroleum, or from one or more synthetic hydrocarbons sources such as catalytic and/or non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed hydrocarbon can include one or more of ethane, propane, butanes, saturated and unsaturated $C_6$ hydrocarbon, including those derived from one or more of Fischer-Tropsch synthesis products, shale gas, biogas, associated gas, natural gas and mixtures or components thereof, steam cracked gas oil and residues, gas oils, heating oil, jet fuel, diesel, kerosene, gasoline, naphtha (including coker naphtha, steam cracked naphtha, and catalytically cracked naphtha), hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, $C_4$-residue admixture, naphtha-residue admixture, cracked feed, coker distillate streams, and hydrocarbon streams derived from plant or animal matter.

Diluent, when present, is typically included in the pyrolysis feed in an amount ≤60 wt. % based on the weight of the feed, e.g., ≤50 wt. %, such as ≤40 wt. %, or ≤30 wt. %, or ≤20 wt. %, or ≤10 wt. %, or in the range of from 10 wt. % to 50 wt. %. Diluent is also suitable for use as a sweep gas, e.g., for (i) removing at least a portion of any pyrolysis product in the reactor after the pyrolysis mode and/or after regeneration mode and/or (ii) adjusting the reactor's temperature profile—heat carried by the sweep gas from warmer regions of the reactor for transfer to cooler regions will increase the temperature of the cooler regions and further lessen or prevent sharp gradients in the reactor temperature profile.

Those skilled in the art will appreciate that feed flow rate will depend on factors such as feed composition, reactor volume, pyrolysis conditions, etc. Accordingly, the invention can be carried out over a very wide range of feed flow rates, e.g., at a flow rate ≥0.001 kg/s, such as ≥0.1 kg/s, or ≥10 kg/s, or ≥100 kg/s, or more.

A flow of the pyrolysis feed is conducted to the regenerative pyrolysis reactor during pyrolysis mode in an average flow direction (for convenience, "forward flow") that is substantially opposed to that of oxidant flow (for convenience, "reverse flow") as shown in FIG. 1. During pyrolysis mode, at least a portion of the feed hydrocarbon is pyrolyzed to produce a pyrolysis product. Certain pyrolysis conditions that are useful for pyrolyzing the specified pyrolysis feeds will now be described in more detail. The invention is not limited to these pyrolysis conditions, and this description is not meant to foreclose the use of other pyrolysis conditions.

The pyrolysis conditions in the pyrolysis zone during pyrolysis time interval $t_P$ generally include $T_p≤1673K$ (1400° C.), $T_{av}≤1473K$ (1200° C.), and an average total pressure ≥0 psig (1.01 bar). Total gas residence time in the pyrolysis zone is generally ≤0.4 seconds to decrease the conversion to coke of desired products such as light olefin. Typically, the pyrolysis conditions include $T_p≤1473K$, e.g., ≤1373K, such as ≤1273K or in the range of from 1273K to 1673K; $T_{av}≤1373K$, e.g., ≤1273K, such as ≤1173K, or in the range of from 1173K to 1373K, or 1198K to 1348K; and a feed hydrocarbon partial pressure ≥0.48 bar (48 kPa), or ≥0.69 bar (69 kPa), or ≥1.38 bar (138 kPa), or ≥2.07 bar (207 kPa). The average total pressure is typically ≥0.34 barg (34 kPag), or ≥1.03 barg (103 kPag), or ≥2.76 barg (276 kPag), or ≥5.52 barg (552 kPag), or ≥8.27 barg (827 kPag). Particularly when the pyrolysis feed includes diluent, the average total pressure can be ≥10.34 barg (1034 kPag), or ≥20.68 barg (2068 kPag), or ≥34.47 barg (3447 kPag). Total gas residence time in the pyrolysis zone is typically ≤0.2 second; preferably ≤0.15 second or ≤0.1 second; or in the range of 0.001 second to 0.4 second, or in the range of 0.01 second to 0.4 second, or in the range of 0.01 second to 0.2 second. For example, the pyrolysis feed can be passed through thermal mass 1 at a total gas residence time at a bulk gas temperature ≥800° C. that is ≤0.100 second, such as ≤0.060 second, such as ≤0.040 second, or in the range of 0.001 second to 0.100 second, or in the range of 0.002 second to 0.060 second, or in the range of 0.002 second to 0.040 second. Typically $T_p$ and/or $T_{av}$ decrease by ≤100K, e.g., ≤75K, such as ≤50K, or ≤25K, or ≤10K, or ≤5K, for a $t_P \geq 1$ second, e.g., ≥2 seconds, such as ≥5 seconds, or ≥10 seconds, or ≥20 seconds, or ≥30 seconds, or even ≥1 minute or more. Although high-severity pyrolysis conditions can be used, it is typical to use low severity conditions. Regions of substantially-constant temperature along the length of the pyrolysis zone are typically avoided. Sharp gradients in the bulk gas temperature profile within the pyrolysis zone are also typically avoided.

When it is desired to keep $T_p$ and/or $T_{av}$ from decreasing by no more than about 100K, and preferably ≤75K during $t_P$, the OFA of at least thermal mass 1 should be ≤55%, e.g., ≤45%, such as ≤40%, or ≤35%. Typically, the OFA of thermal mass 1 is in the range of about 10% to 55%, e.g., 10% to 50%, such as 10% to 45%, or 10% to 35%. Smaller values of OFA, which lead to a smaller decrease in the temperatures $T_p$ and $T_{av}$ during $t_P$, are typically desired at relatively large values of $T_p$, e.g., ≥1273K, such as ≥1473K, or ≥1573K. For example, when $T_{av}$ exceeds 1173K, it is beneficial for the thermal mass to have an OFA of ≤45%. When $T_{av}$ exceeds 1273K, it is beneficial for the thermal mass to have an OFA of ≤35%, and when $T_{av}$ exceeds 1373K, it is beneficial for the thermal mass to have an OFA of ≤25%. Stated another way, when $T_p$ exceeds 1273K, it is beneficial for $\Delta T_p$ and/or $\Delta T_{av}$ to be ≤50K, when $T_p$ exceeds 1372K, it is beneficial for $\Delta T_p$ and/or $\Delta T_{av}$ to be ≤40K, and when $T_p$ exceeds 1473K, it is beneficial for $\Delta T_p$ and/or $\Delta T_{av}$ to be ≤20K.

The duration of pyrolysis mode operation $t_P$ can be, e.g., ≥1 second, such as ≥2 seconds, or ≥5 seconds, or ≥10 seconds, or ≥20 seconds, or ≥30 seconds, or even ≥1 minute or more. For example, $t_P$ can be in the range of from 1 second to 30 seconds, e.g., 2 seconds to 15 seconds, such as 2 seconds to 10 seconds. Optionally, conventional methods are used to achieve these ranges of $t_P$, e.g., using one or more poppet valves and/or hydrodynamic valving to regulate the flows of feed and process gas during pyrolysis mode and the flows of heating mixture and combustion product during regeneration mode.

The reactor's bulk gas temperature profile typically maintains a substantially constant shape (although decreasing in magnitude) during these relatively long $t_P$ values. Referring again to FIG. 3, the solid line represents the bulk gas temperature profile at the start of pyrolysis mode ($t_1$), and the dashed line represents the bulk gas temperature profile at the end of pyrolysis mode ($t_2$). At any time during the pyrolysis variations in the bulk gas temperature are typically ≤140K within any pyrolysis zone segment having a length ≤10% of $l_C$, e.g., ≤100K, such as ≤50K. Typically, temperature variations are ≤75K within any segment of thermal mass 1 that has a length ≤10% of $l_B$, e.g., ≤50K, such as ≤25K. In certain aspects, the peak gas temperature $T_p$ during pyrolysis is displaced away from the reactor's center. For example, the length of the pyrolysis zone's downstream segment $l_A$ is less than that of the upstream segment $l_B$, e.g., at least 10% less, such as at least 25% less, or at least 50% less. The total length of the pyrolysis zone $l_C$ is the sum of $l_A$ and $l_B$. Typically, $l_C$ is in the range of from 10% to 50% of the total length of reactor 50, e.g., in the range of 20% to 40%. For example, $l_c$ can be in the range of from 20% to 40% of $L_1+L_2+L_3+L_4$. The locations of the terminal ends of $l_A$ and $l_B$ are determined by the minimum temperature $T_{MIN}$ needed for appreciable (≥10 wt. %) conversion of the selected feed under the specified pyrolysis conditions, e.g., $T_{MIN}$ in the range of 773K to 1273K.

In certain aspects, the bulk gas temperature profile at the start of pyrolysis increases substantially monotonically as shown in FIG. 3 from a first temperature ($T_1$) proximate to the first aperture 3 of thermal mass 1 to a second temperature ($T_2$) proximate to the second aperture 5. The peak gas temperature $T_p$, located at a position that is at or downstream of face 5, is greater than $T_2$. $T_p$–$T_2$ at the start of pyrolysis is typically in the range of from 10K to 400K, or 25K to 300K, or 50K to 200K. $T_p$ decreases during the pyrolysis by an amount ($\Delta T_p$) that is ≤100° C. Typically, the location of $T_p$ within the pyrolysis zone remains substantially constant during the pyrolysis. Substantially constant in this context means that the location of $T_p$ changes during pyrolysis mode from its initial position by ≤+/–20% of $l_c$, e.g., ≤+/–15%, such as ≤+/–10%, or typically ≤+/–5%. $T_1$ is less than $T_2$ during pyrolysis, e.g., $T_1$ at the start of pyrolysis can be ≤1673K, e.g., ≤1573K, such as ≤1473K, or ≤1373K, or ≤1273K. $T_2$–$T_1$ at the start of pyrolysis is typically in the range of from 50K to 500K, such as from 100K to 400K, or 100K to 300K. In particular aspects, the pyrolysis conditions at the start of pyrolysis include $T_1 \leq 1173K$, e.g., ≤1023K, such as ≤773K; $T_2$ in the range of from 1248K to 1373K, $T_p \geq 1423K$, and $T_{MIN}$–$T_1$ in the range of from 10K to 400K, or 25K to 300K, or 50K to 200K. Although the bulk gas temperature profile at the start of $t_P$ is substantially congruent with that at the end of $t_P$, the location in the pyrolysis zone at which appreciable pyrolysis is achieved translates during $t_P$ from reference position $R_1$ toward aperture 5 to reference position $R_2$ at the end of $t_P$ ($t=t_2$). At $t_2$ the bulk gas temperature profile increases substantially monotonically from a first temperature ($T_3$) proximate to first aperture 3 to a second temperature ($T_4$) proximate to the second aperture 5. $T_3$ is ≤$T_1$ and $T_4$ is in the range of from $T_2$ to ($T_2$–100K), e.g., $T_2$ to ($T_2$–75K), such as $T_2$ to ($T_2$–50K). The reference location $R_1$ is positioned, e.g., within $0.2*L_1$ and $0.4*L_1$ of the second aperture.

The process gas conducted away from the reactor during pyrolysis mode comprises a range of desired hydrocarbon products, including a desirable range of $C_2$-$C_5$ olefin. Typically, one or more of the desired hydrocarbon compounds is separated from the process gas, e.g., for storage and/or further processing. Typically, the process gas comprises molecular hydrogen; methane; ethane; ethylene; propane; propylene; butanes; butenes; butadiene; $C_5$ hydrocarbon, including normal, iso, and cyclo $C_5$ olefin and paraffin, and $C_{6+}$ hydrocarbon, including aromatics and normal, iso, and cyclo $C_{6+}$ olefin and paraffin. For example, particularly when the feed includes ethane, the pyrolysis product can comprise 2 wt. % to 10 wt. % methane, 50 wt. % to 95 wt. % ethylene, 0.2 wt. % to 1 wt. % propylene, 0.1 wt. % to 5 wt. % butadiene, and up to about 3 wt. % benzene, based on the weight of the pyrolysis product. As may be appreciated, these very desirable compositional ranges for the identified hydrocarbon compounds are achieved not only at the start of pyrolysis mode, but during the duration of $t_P$.

The process gas is compressed in at least one compression stage which includes at least one process gas compressor. The process gas compressor utilizes at least a portion of the first and second shaft powers produced by the power generator. Suitable process gas compressors will now be described in more detail. The invention is not limited to these compressors, and this description is not meant to foreclose the use of other compressors within the broader scope of the invention.

Alternative Configuration—Steam Cracking

Another option for performing a pyrolysis reaction is to use a conventional steam cracker configuration. The steam cracker furnace generally includes a convection section and a radiant section. The radiant section includes a plurality of tubular members which are typically referred to as "radiant tubes". Conventionally, the radiant tubes are located proximate to one or more fired heaters, e.g., burners, in the radiant section which heat the outer surface of the furnace tubes. This radiant section corresponds to a combustion zone for the furnace. Hot combustion gases exit the radiant section and are introduced into the convection section. The convection section also includes tubular members, typically referred to as "convection tubes". The hot gases from the radiant section heat the outer surfaces of the convection tubes and then exit the convection section.

Conventional steam cracking processes typically produce light olefin by hydrocarbon pyrolysis during pyrolysis mode. Coke and other deposits which form during pyrolysis mode are removed from the furnace internals during regeneration (decoking) mode. During pyrolysis mode, a hydrocarbon-containing feed is introduced into the convection tubes for feed preheating. Feed preheating is carried out in segments of the convection tubes located in an upper region of the convection section. Steam is combined with the preheated feed, and the steam-feed mixture is further heated in segments of the convection tubes located in a lower region of the convection section. The heated feed-steam mixture is introduced into the heated furnace tubes in the radiant section, and heat transferred from the furnace tube to the mixture results in the pyrolysis of at least a portion of the feed to produce a process gas comprising light olefin. During regeneration mode, a flow of oxygenate-containing decoking fluid (e.g., a gaseous steam-air mixture) is substituted for the hydrocarbon-containing feed, and the burners continue to heat the radiant and convection sections. The decoking fluid is conducted through the heated convection tubes, heated radiant tubes, and associated furnace piping, internals, etc., to at least partly remove deposited coke. After sufficient coke removal is achieved, the steam cracking furnace is returned to pyrolysis mode operation.

Representative Process Gas Compressor

In the compressor stage, the process gas is typically compressed to pressure in the range of from 20 bar (2000 kPa) to 40 bar (4000 kPa) in a centrifugal compressor powered by shaft power. Typically, the process gas compressor includes at least four sections, with each section in sequence providing an increase in pressure over its preceding sections. Cooling is typically employed between the sections, e.g., to prevent compressor damage, to prevent fouling resulting from diolefin polymerization, and to facilitate separation of process gas constituents. The invention is compatible with conventional process gas compressors, but the invention is not limited thereto.

All patents, test procedures, and other documents cited herein, including priority documents, are fully incorporated by reference to the extent such disclosure is not inconsistent. It is not intended that the scope of the claims appended hereto be limited to the descriptions set forth herein but rather that the claims be construed as encompassing all patentable features which reside herein, including all features which would be treated as equivalents thereof by those skilled in the relevant art. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group consisting of," or "is" preceding the recitation of the composition, component, or components, and vice versa. Pressure values are absolute (bar, kPa, psi, or psia) unless expressly indicated as gauge (barg, kPag, psig).

The invention claimed is:

1. A process for producing and compressing a process gas, the process comprising:
   separating air to form at least an oxygen-containing stream, the oxygen-containing stream comprising 90 vol. % or more $O_2$;
   combusting at least a portion of a fuel with at least a portion of the oxygen-containing stream in the presence of at least a portion of a recycle stream to produce a heated working fluid, the recycle stream comprising 80 vol. % or more $CO_2$;
   expanding the heated working fluid to produce shaft power and a decompressed working fluid comprising at least $CO_2$ and $H_2O$;
   pyrolyzing at least a portion of a hydrocarbon-containing feed to produce a process gas comprising ethylene;
   separating the decompressed working fluid by performing a series of cooling and compressing steps to form a water stream and a $CO_2$-containing stream, the $CO_2$ in the decompressed working fluid and the $CO_2$-containing stream being in a supercritical state during the series of cooling and compressing steps;
   transferring at least part of the shaft power a) to a process gas compressor to compress the process gas, b) to a refrigeration compressor to cool the process gas, c) to a refrigeration compressor to cool the decompressed working fluid in a cooling step from the series of cooling and compressing steps, or d) a combination of two or more of a), b) and c); and
   compressing at least a portion of the $CO_2$-containing stream to form a compressed $CO_2$-containing stream, the recycle stream comprising at least a first portion of the compressed $CO_2$-containing stream.

2. The process of claim 1, wherein the decompressed working fluid comprises 90 vol. % or more of $CO_2$ and $H_2O$.

3. The process of claim 1, wherein the transfer of the shaft power comprises direct power transfer, indirect power transfer, or a combination thereof.

4. The process of claim 1, wherein the fuel comprises one or more of (i) natural gas, (ii) hydrocarbon in the natural gas, (iii) hydrocarbon separated from the natural gas and/or derived from the natural gas, (iv) natural gas condensate, (v) hydrocarbon in the natural gas condensate, (vi) hydrocarbon separated from the natural gas condensate and/or derived from the natural gas condensate, (vii) crude oil, (viii) hydrocarbon in the crude oil, (viii) hydrocarbon separated from the crude oil and or derived from the crude oil, and (ix) molecular hydrogen.

5. The process of claim 1, wherein the feed comprises >10 wt. % $C_2$+ hydrocarbon.

6. The process of claim 1, wherein the compressed $CO_2$-containing stream comprises a pressure of 200 bar or more.

7. The process of claim 1, wherein the at least a portion of the shaft power is transferred a) to a process gas compressor to compress the process gas, b) to a refrigeration compressor to cool the process gas, or e) a combination of a) and b).

8. The process of claim 1, further comprising transferring at least a second portion of the shaft power to a compressor for i) performing the compressing in the series of cooling and compressing steps, ii) refrigeration to perform at least a portion of the cooling in the series of cooling and compressing steps, iii) performing the compressing of the $CO_2$-containing stream, or iv) a combination of two or more of i), ii) and iii).

9. The process of claim 1, wherein the pyrolyzing is carried out in at least one steam cracking furnace.

10. The process of claim 1, wherein the pyrolyzing is carried out in at least one reverse-flow thermal pyrolysis reactor.

11. The process of claim 1, wherein the fuel comprises at least a portion of a tail gas recovered from the process gas.

12. The process of claim 1, wherein at least a portion of the water stream is (i) fed into pyrolyzing step to mix with the hydrocarbon-containing feed; (ii) heated to generate steam; (iii) used as an indirect cooling medium; (iv) used as a quenching medium; and (iv) fed into a hydrocarbon-containing stream as a diluent.

13. The process of claim 1, further comprising:
recovering an ethylene stream from the process gas stream;
contacting at least a portion of the ethylene stream with at least a portion of the oxygen-containing stream to produce an oxidized stream; and
producing a monoethylene glycol product from the oxidized stream.

14. The process of claim 13, wherein the oxidized stream comprises ethylene oxide, and the step of producing the monoethylene glycol product comprises contacting the ethylene oxide with the $CO_2$ sourced from the compressed $CO_2$ stream and/or the $CO_2$-containing stream.

15. The process of claim 1, further comprising at least one of the following:
supplying a portion of the compressed $CO_2$ stream to a storage;
conducting away a portion of the compressed $CO_2$ stream in a pipeline;
using a portion of the compressed $CO_2$ stream to extract a hydrocarbon source material, and deriving at least a portion of the hydrocarbon-containing feed from the hydrocarbon source material.

16. The process of claim 1, wherein the pyrolyzing is performed under pyrolysis conditions comprising a temperature in the range of from 773K to 1773K, a total pressure ≥34 kPag, and a hydrocarbon partial pressure of ≥48 kPa.

17. The process of claim 1, further comprising carrying out the pyrolyzing of step for a time interval $t_P$, and regenerating a reverse-flow thermal pyrolysis reactor during a time interval $t_R$, wherein $t_P$ and $t_R$ are substantially non-overlapping time intervals.

18. The process of claim 1,
wherein combusting at least a portion of the fuel comprises combusting a first portion of the fuel with a first portion of the oxygen-containing stream in the presence of a first portion of the recycle stream in a first combustion zone to produce a first heated working fluid and combusting a second portion of the fuel with a second portion of the oxygen-containing stream in the presence of a second portion of the recycle stream in a second combustion zone to produce a second heated working fluid,
wherein the first heated working fluid is expanded to produce first shaft power, and
wherein the second heated working fluid expanded to produce second shaft power.

* * * * *